United States Patent
Peyman

(10) Patent No.: US 10,300,121 B2
(45) Date of Patent: *May 28, 2019

(54) EARLY CANCER DETECTION AND ENHANCED IMMUNOTHERAPY

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 0 days.

This patent is subject to a terminal disclaimer.

(21) Appl. No.: 15/853,821

(22) Filed: Dec. 24, 2017

(65) Prior Publication Data
US 2018/0133298 A1    May 17, 2018

Related U.S. Application Data

(63) Continuation-in-part of application No. 15/143,981, filed on May 2, 2016, now Pat. No. 9,849,092, which is a continuation-in-part of application No. 14/976,321, filed on Dec. 21, 2015, now Pat. No. 10,136,820.

(60) Provisional application No. 62/577,485, filed on Oct. 26, 2017, provisional application No. 62/569,592, filed on Oct. 8, 2017.

(51) Int. Cl.
| | |
|---|---|
| *A61K 9/50* | (2006.01) |
| *A61K 39/00* | (2006.01) |
| *A61K 41/00* | (2006.01) |
| *A61K 47/68* | (2017.01) |
| *A61K 47/69* | (2017.01) |
| *A61K 35/17* | (2015.01) |
| *A61K 49/22* | (2006.01) |
| *C07K 16/30* | (2006.01) |
| *A61B 5/00* | (2006.01) |
| *A61N 5/06* | (2006.01) |
| *A61P 35/00* | (2006.01) |
| *A61K 39/395* | (2006.01) |
| *A61M 1/34* | (2006.01) |

(52) U.S. Cl.
CPC ........ *A61K 39/0011* (2013.01); *A61B 5/0095* (2013.01); *A61K 35/17* (2013.01); *A61K 39/39558* (2013.01); *A61K 41/0028* (2013.01); *A61K 41/0052* (2013.01); *A61K 47/6851* (2017.08); *A61K 47/6929* (2017.08); *A61K 49/221* (2013.01); *A61K 49/222* (2013.01); *A61N 5/062* (2013.01); *A61P 35/00* (2018.01); *C07K 16/30* (2013.01); *C07K 16/3061* (2013.01); *A61K 2039/5154* (2013.01); *A61K 2039/545* (2013.01); *A61M 1/3496* (2013.01)

(58) Field of Classification Search
None
See application file for complete search history.

(56) References Cited

U.S. PATENT DOCUMENTS

| | | |
|---|---|---|
| 3,993,754 A | 11/1976 | Rahman et al. |
| 4,235,871 A | 11/1980 | Papahadjopoulos et al. |
| 4,522,803 A | 6/1985 | Lenk et al. |
| 4,586,512 A | 5/1986 | Do-huu et al. |
| 4,620,546 A | 11/1986 | Aida et al. |
| 4,658,828 A | 4/1987 | Dory |
| 4,891,043 A | 1/1990 | Zeimer et al. |
| 5,094,854 A | 3/1992 | Ogawa et al. |
| 5,118,666 A | 6/1992 | Habener |
| 5,149,319 A | 9/1992 | Unger |
| 5,203,782 A | 4/1993 | Gudov et al. |
| 5,220,181 A | 6/1993 | Kanal et al. |
| 5,545,618 A | 8/1996 | Buckley et al. |
| 5,935,942 A | 8/1999 | Zeimer |
| 5,976,502 A | 11/1999 | Khoobehi et al. |
| 6,179,767 B1 | 1/2001 | Ziegler et al. |
| 6,197,022 B1 | 3/2001 | Baker |
| 6,248,727 B1 | 6/2001 | Zeimer |
| 6,552,053 B2 | 4/2003 | Sun et al. |
| 6,566,595 B2 | 5/2003 | Suzuki et al. |
| 6,583,111 B1 | 6/2003 | DiMarchi et al. |
| 6,641,553 B1 | 11/2003 | Chee et al. |
| 6,984,655 B1 | 1/2006 | Mori et al. |
| 7,638,139 B2 | 12/2009 | Peyman |
| 8,324,344 B2 | 12/2012 | Kisiel |

(Continued)

OTHER PUBLICATIONS

Gao et al., Autologous tumor lysate-pulsed dendritic cell immunotherapy with cytokine-induced killer cells improves survival in gastric and colorectal cancer patients. PLoS One, vol. 9, issue 4 (2014), pp. 1-9.
Min et al. Lentivirus-Mediated sFlt-1 Gene Fragment Transfer Suppresses Retinal Neovascularization. Current Eye Research 34 (2009) 401-410.
Mulder et al. Quantum dots for multimodal molecular imaging of angiogenesis. Angiogenesis 13 (2010) 131-134.
Singerman. Combination therapy using the small interfering RNA bevasiranib. Retina 2009, Abstract Only.
Smith et al., Bioconjugated Quantum Dots for In Vivo Molecular and Cellular Imaging. Adv. Drug Deliv. Rev. 60 (2008) 1226-1240.
You et al. Incorporation of quantum dots on virus in polycationic solution. Int. J. Nanomedicine 1 (2006) 59-64.

(Continued)

*Primary Examiner* — Michael D Burkhart
(74) *Attorney, Agent, or Firm* — The Law Office of Patrick F. O'Reilly III, LLC

(57) ABSTRACT

A method of therapy for a tumor or other pathology by administering a combination of thermotherapy, immunotherapy, and vaccination optionally combined with gene delivery. The combination therapy beneficially treats the tumor and prevents tumor recurrence, either locally or at a different site, by boosting the patient's immune response both at the time or original therapy and/or for later therapy. With respect to gene delivery, the inventive method may be used in cancer therapy, but is not limited to such use; it will be appreciated that the inventive method may be used for gene delivery in general. The controlled and precise application of thermal energy enhances gene transfer to any cell, whether the cell is a neoplastic cell, a pre-neoplastic cell, or a normal cell.

16 Claims, No Drawings

(56) References Cited

U.S. PATENT DOCUMENTS

| | | | |
|---|---|---|---|
| 2002/0174743 | A1 | 11/2002 | Mukherjee et al. |
| 2003/0014089 | A1 | 1/2003 | Chow et al. |
| 2003/0022374 | A1 | 1/2003 | Greenbaum et al. |
| 2004/0003839 | A1 | 1/2004 | Curtain |
| 2005/0004625 | A1 | 1/2005 | Chow |
| 2006/0173362 | A1 | 8/2006 | Toms et al. |
| 2010/0185260 | A1 | 7/2010 | Olson |
| 2010/0211146 | A1 | 8/2010 | Strowbridge et al. |
| 2011/0270153 | A1 | 11/2011 | Olson |
| 2011/0287035 | A1 | 11/2011 | Peyman |
| 2012/0226139 | A1 | 9/2012 | Peyman |
| 2015/0202466 | A1 | 7/2015 | Gertner |
| 2016/0022976 | A1 | 1/2016 | Peyman |
| 2018/0133298 | A1* | 5/2018 | Peyman |

OTHER PUBLICATIONS

Wang et al. Nucleic Acid Conjugated Nanomaterials for Enhanced Molecular Recognition. ACS Nano 3 (2009) 2451-2460.

Lee et al. The retinoblastoma susceptibility gene encodes a nuclear phosphoprotein associated with DNA binding activity. Nature, 329 (1987) 642-645.

Tomczak et al. Designer polymer-quantum dot architectures. Progress in Polymer Science, 34 (2009) 393-430.

Duan and Nle. Cell-penetrating quantum dots based on multivalent and endosome-disrupting surface coatings. J. Am. Chem. Soc. 129 (2007) 3333-3338.

Kim and Taton. Multicomponent nanoparticles via self-assembly with cross-linked block copolymer surfactants. Langmuir, 23 (2007) 2198-2202.

Pan et al. Silica Cross-linked Micelles Loading with Silicon Nanoparticles: Preparation and Characterization. ACS Appl. Mater. Interfaces 5 (2013) 7042-7049.

Lv et al., Surface modification of quantum dots and magnetic nanoparticles with PEG-conjugated chitosan derivatives for biological applications. Chemical Papers 67 (2013) 1404-1413.

Suzuki et al. Quantum Dot FRET Biosensors that Respond to pH, to Proteolytic or Nucleolytic Cleavage, to DNA Synthesis, or to a Multiplexing Combination. J. Am. Chem. Soc. 130 (2008) 5720-5725.

Huang et al. Intermolecular and Intramolecular Quencher Based Quantum Dot Nanoprobes for Multiplexed Detection of Endonuclease Activity and Inhibition, Anal. Chem. 83 (2011) 8913-8918.

Akbarzadeh et al. Liposome: classification, preparation, and applications. Nanoscale Research Letters 8:102 (2013) 1-9.

Sander et al. CRISPR-Cas systems for editing, regulating and targeting genomes. Nature Biotechnology 32:4 (2014) 347-355.

Peyman et al. A High-Resolution 3D Ultrasonic System for Rapid Evaluation of the Anterior and Posterior Segment. Ophthalmic Surgery, Lasers & Imaging 43 (2012) 143-151.

Andor Technology, "Transport Across the Nuclear Membrane Using Quantum Dots," Aug. 23, 2011, available at http://www.andor.com/company/news/?docID=1224.

Boyden, "Optogenetics: Using Light to Control the Brain," The Dana Foundation, Nov. 30, 2011, available at http://www.dana.org/news/cerebrum/detaiLaspx?id=34614.

Buchen, "Illuminating the Brain," Nature, vol. 465, May 6, 2010, pp. 26-28.

Dixit et al., "Quantum Dot Encapsulation in Viral Capsids," Nano Letters, vol. 6, No. 9 (2006); pp. 1993-1999.

Deisseroth, "Optogenetics," Nature Methods, Published online Dec. 20, 2010, available at http://www.stanford.edu/group/dlab/papers/deisserothnature2010.pdf.

Deisseroth, "Optogenetics: Controlling the Brain with Light [Extended Version]," Scientific American, Published online Oct. 20, 2010, available at http://www.scientificamerican.com/article.cfm?id=optogenetics-controlling.

Dubertret et al., "In vivo Imaging of Quantum Dots Encapsulated in Phospholipid Micelles," Science, vol. 298, No. 5599 (2002), pp. 1759-1762.

Gill et al., "Fluorescence Resonance Energy Transfer in CdSe/ZnS-DNA Conjugates: Probing Hybridization and DNA Cleavage," J. Phys. Chem. B., vol. 109 (2005), pp. 23175-23179.

Joo et al., "Enhanced Real-Time Monitoring of Adeno-Associated Virus Trafficking by Virus-Quantum Dot Conjugates," ACSNano, vol. 5, issue 5 (2011); pp. 3523-3535.

Michalet et al., "Quantum Dots for Live Cells, in Vivo Imaging, and Diagnostics," Science, 307, No. 5709 (2005), pp. 538-544.

Yizhar et al., "Optogenetics in Neural Systems," Neuron, vol. 71 (2011), 9-34.

Zhang et al., "Optogenetic interrogation of neural circuits: technology for probing mammalian brain structures," Nature Protocols, vol. 5, No. 3 (2010), pp. 439-456.

Aguilera et al. "Systemic in vivo distribution of activatable cell penetrating peptides is superior to cell penetrating peptides," Integr Biol (Camb), vol. 1 , No. 5-6 (2009), pp. 371-381.

Kelley. "What Clinicians Need to Know About Molecular Markers in Solid Tumors" Aug. 6, 2010, available at http://www.medscape.org/viewarticle/725989.

Nguyen et al. "Surgery with molecular fluorescence imaging using activatable cell-penetrating peptides decreases residual cancer and improves survival," Proc. Nat. Acad. Sci., 107 (2010) 4317-4322.

Olson et al. "In vivo characterization of activatable cell penetrating peptides for targeting protease activity in cancer," Integr Bioi, 1 (2009) pp. 382-393.

Olson et al. "Activatable cell penetrating peptides linked to nanoparticles as dual probes for in vivo fluorescence and MR imaging of proteases," Proc. Nat. Acad. Sci. 107 (2010) 4311-4316.

Hoare et al. "A Magnetically-Triggered Composite Membrane for On-Demand Drug Delivery," Nano Lett. 9 (2009) 3651-3657.

Mornet et al., Magnetic nanoparticle design for medical diagnosis and therapy, J. Mater. Chem., 14 (2004) 2161-2175.

Sexton et al. "A Protective Vaccine Delivery System for In Vivo T Cell Stimulation Using Nanoengineered Polymer Hydrogel Capsules," ACS Nano, vol. 3, No. 11 (2009), pp. 3391-3400.

Alavarez-Lorenzo et al., "Temperature-sensitive chitosan-poly(N-isopropylacrylamide) interpenetrated networks with enhanced loading capacity and controlled release properties" J. Controlled Release 102(3), (2005) 629-641.

Balasubramaniam et al., "Poly(N-isopropylacrylamide)-Coated Superaramagnetic Iron Oxide Nanoparticles: Relaxometric and Fluorescence Behavior Correlate to Temperature-Dependent Aggregation" Chem. Mater., 2011, 23, 3348-3356.

Benyettou et al., "Magnetoliposome for alendronate delivery" J. Mater. Chem., 21 (2011) 4813-4820.

Budgin et al. "Functionalization of Magnetic Nanoparticles with Amphiphilic Block Copolymers: Self-Assembled Thermoresponsive Submicrometer Particles" Langmuir 28 (2012) 4142-4151.

Farokhzad et al., "Impact of Nanotechnology on Drug Delivery" ACS Nano 3(1) 2009, 16-20.

Filipa et al., "Polyelectrolyte-Coated Unilamellar Nanometer-Sized Magnetic Liposomes" Langmuir 2009, 25(12), 6793-6799.

Pothayee et al., "Magnetic Block Ionomer Complexes for Potential Dual Imaging and Therapeutic Agents" Chem. Mater. 2012, 24, 2056-2063.

Tai et al. "Thermosensitive liposomes entrapping iron oxide nanoparticles for controllable drug release" Nanotechnology 20 (2009) 135101 (9 pages).

Xu et al. "Controlled Release and Assembly of Drug Nanoparticles via pH-Responsive Polymeric Micelles: A Theoretical Study" J. Phys. Chem. B, 2012, 116 (20), 6003-6009.

Booth et al. Exosomes and HIV Gag bud from endosome-like domains of the T cell plasma membrane. The Journal of Cell Biology, vol. 172, No. 6, Mar. 13, 2006, 923-935.

Heath et al., Varying Polymer Architecture to Deliver Drugs AAPS J. 9 (2007) Nanotechnology and Drug Delivery, article 26 (http://www.aapsi.org) E235-E240.

Jamagin et al. Treatment of cholangiocarcinoma with oncolytic herpes simplex virus combined with external beam radiation therapy. Cancer Gene Therapy 13 (2006) 326-334.

Ding et al., Farnesyltransferase inhibitor tipifamib inhibits Rheb prenylation and stabilizes Bax in acute myelogenous leukemia cells. Haematologica 99 (2014) 60-69.

(56) References Cited

OTHER PUBLICATIONS

Kleiner et al. Farnesyl and geranylgeranyl transferase inhibitors: an anti-inflammatory effect. Comment to "Inhibition of protein geranylgeranylation and farnesylation protects against graft-versus-host disease via affects on CD4 effector T cells" haematological 98 (2013) e44-e45.
Karp et al. Multi-institutional phase 2 clinical and pharmacogenomic trial of tipifarnib plus etoposide for elderly adults with newly diagnosed acute myelogenous leukemia. Blood 119 (2012) 55-63.
Hong et al. Phase I Trial of a Combination of the Multikinase Inhibitor Sorafenib and the Farnesyltransferase Inhibitor Tipifarnib in Advanced Malignancies. Clin Cancer Res 15 (2009), 7061-7068.
Kurzrock et al. Phase I Study of Alternate-Week Administration of Tipifarnib in Patients with Myelodysplastic Syndrome. Clin Cancer Res 14 (2008) 509-514.
Haferlach. Molecular Genetic Pathways as Therapeutic Targets in Acute Myeloid Leukemia. (2008) 400-411.
Armand et al. The Emerging Role of Targeted Therapy for Hematologic Malignancies: Update on Bortezomib and Tipifarnib. The Oncologist 12 (2007) 281-290.
Yanamandra et al. Tipifarnib and Bortezomib Are Synergistic and Overcome Cell Adhesion-Mediated Drug Resistance in Multiple Myeloma and Acute Myeloid Leukemia. Clin Cancer Res 12 (2006) 591-599.
Beaupre et al. R115777 induces Ras-independent apoptosis of myeloma cells via multiple intrinsic pathways. Mol Cancer Ther 3 (2004) 179-186.
Leite et al. PE and PS Lipids Synergistically Enhance Membrane Poration by a Peptide with Anticancer Properties. Biophysical Journal 109 (2015) 936-947.
Bakalova et al., "Quantum Dot-Conjugated Hybridization Probes for Preliminary Screening of siRNA Sequences" J. Am. Chem. Soc., (2005), 127 (32), pp. 11328-11335.
Derfus et al. "Targeted Quantum Dot Conjugates for siRNA Delivery" Bioconjugate Chem., vol. 18, No. 5 (2007) pp. 1391-1396.
Ebenstein et al. "Combining atomic force and fluorescence microscopy for analysis of quantum-dot labeled protein-DNA complexes" J. Molecular Recognition, vol. 22, issue 5 (2009), pp. 397-402.
Gill et al. "Fluorescence Resonance Energy Transfer in CdSe/ZnS-DNA Conjugates: Probing Hybridization and DNA Cleavage" J. Phys. Chem. B, vol. 109, (2005), pp. 23715-23719.
Joo et al. "Enhanced Real-Time Monitoring of Adeno-Associated Virus Trafficking by Virus-Quantum Dot Conjugates" ACS Nano, vol. 5, No. 5 (2011), pp. 3523-3535.
Lim et al. "Specific Nucleic Acid Detection Using Photophysical Properties of Quantum Dot Probes" Anal. Chem., vol. 82, No. 3 (2010), 886-891.
Mossman "Quantum dots track who gets into cell nucleus" Physorg.com, Sep. 2, 2010, available at http://www.physorg.com/news202628740.html.
You et al. "Incorporation of quantum dots on virus in polycationic solution" Int. J. Nanomedicine, vol. 1, No. 1 (2006), pp. 59-64.
Anscombe "Quantum Dots: Small Structures Poised to Break Big" Photonics Spectra, Jul. 2005, pp. 94-96.
Mali et al. "Intravitreous Injection of a Membrane Depolarization Agent Causes Retinal Degeneration via Matrix Metalloproteinase-9" Investigative Ophthalmology and Visual Science, vol. 46, No. 6 (2005), pp. 2125-2132.
Greenbaum et al. "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istanbul, Turkey, vol. 4, pp. 4089-4091.
Aylott "Optical nanosensors-an enabling technology for intracellular measurements" Analyst, vol. 128 (2003), pp. 309-312.
Buck et al. "Optochemical nanosensor PEBBLEs: photonic explorers for bioanalysis with biologically localized embedding" Current Opinion in Chemical Biology, vol. 8 (2004), pp. 540-546.

Fehr et al. "Development and use of fluorescent nanosensors for metabolite imaging in living cells" Biochemical Society Transactions, vol. 23, part 1 (2005), pp. 287-290.
Ferreira et al. "Downstream processing of plasmid DNA for gene therapy and DNA vaccine applications," Tibtech, vol. 18 (2000), pp. 380-387.
Fei et al. "Glucose nanosensors based on redox polymer/glucose oxidase modified carbon fiber nanoelectrodes" Talanta, vol. 65 (2005), pp. 918-924.
Haes et al. "A unified view of propagating and localized surface plasmon resonance biosensors" Anal. Bioanal. Chem, vol. 379 (2004), pp. 920-930.
Cullum et al. "The development of optical nanosensors for biological measurements" Tibtech, vol. 18 (2000), pp. 388-393.
Hauser and Zhang, "Peptides as biological semiconductors," Nature, vol. 468 (2010), p. 516.
Audero et al. Sporadic Autonomic Dysregulation and Death Associated with Excessive Serotonin Autoinhibition. Science, vol. 321 (2008), pp. 130-133.
De Crespigny et al. Magnetic Resonance Imaging Assessment of Cerebral Hemodynamics During Spreading Depression in Rats. Journal of Cerebral Blood Flow and Metabolism, vol. 18 (1998), pp. 1008-1017.
Hohne et al. Acetazolamide prevents hypoxic pulmonary vasoconstriction in conscious dogs. J. Appl. Physiol. vol. 97 (2004), pp. 515-521.
Rio-Portilla et al. REM Sleep Post-Eye Movement Activation. International Journal of Bioelectromagnetism, vol. 10, No. 4 (2008), pp. 192-208.
IBM Press Release, Made in IBM Labs: IBM Scientists Demonstrate World's Fastest Graphene Transistor, Feb. 5, 2010, 1 page.
Kurzwiel Al, Engineers envision 2-dimensional graphene metamaterials and 1-atom-thick optical devices. Jun. 10, 2011, 1 page; internet address: http://www.kurzweilai.net/engineers-envision-2-dimensional-graphene-metamaterials-and-1-atom-thick-optical-devices.
Erogbogbo et al. Plasmonic gold and luminescent silicon nanoplaforms for multimode imaging of cancer cells. Integr. Biol. 5 (2013) 144-150.
Yezhelyev et al., Proton-Sponge-Coated Quantum Dots for siRNA Delivery and Intracellular Imaging. JAm. Chem. Soc. 130 (2008) 9006-9012.
Rajan and Raj. Potential Drug Delivery Applications of Chitosan Based Nanomaterials. I.Re.CH.E. 5 (2013) 145-155.
Song et al., Tumor Cell Targeting Using Folate-Conjugated Fluorescent Quantum Dots and Receptor-Mediated Endocytosis. Clinical Chemistry 55 (2009) 955-963.
Liu et al. Bioconjugated Pluronic Triblock-Copolymer Micelle-Encapsulated Quantum Dots for Targeted Imaging of Cancer: In Vitro and In Vivo Studies. Theranostics 2 (2012) 705-713.
Jin et al. Preparation and Characterization of Highly Fluorescent, Glutathione-coated Infrared Quantum Dots for in Vivo Fluorescence Imaging. Int. J. Mol. Sci. 9 (2008) 20440-2061.
Liu et al., Endocytic Trafficking of Nanoparticles Delivered by Cell-penetrating Peptides Comprised of Nona-arginine and a Penetration Accelerating Sequence, PLOS ONE 8 (2013) e67100, 12 pages.
Liu et al., Intracellular Delivery of Nanoparticles and DNAs by IR9 Cell-penetrating Peptides, PLOS ONE 8 (2013) e64205 (13 pages).
Liu et al., Cell-Penetrating Peptide-Functionalized Quantum Dots for Intracellular Delivery. J. Nanosci. Nanotechnol. 10 (2010) 7897-7905.
Liu et al., Cellular Internalization of Quantum Dots Noncovalentiy Conjugated with Arginine-Rich Cell-Penetrating Peptides. J. Nanosci. Nanotechnol. 10 (2010) 6534-6543.
Xu et al., Nona-Arginine Facilitates Delivery of Quantum Dots into Cells via Multiple Pathways. J. Biomedicine and Biotechnology 2010, Article ID 948543, 11 pages.
Delehanty et al., Self-Assembled Quantum Dot-Peptide Bioconjugates for Selective Intracellular Delivery. Bioconjug Chem 17 (2006) 920-927.
Narayanan et al., Mimicking cellular transport mechanism in stem cells through endosomal escape of new peptide-coated quantum dots. Scientific Reports 3, article No. 2184, 6 pages.

(56) References Cited

OTHER PUBLICATIONS

Ho et al., Combining QD-FRET and Microfluidics to Monitor DNA Nanocomplex Self-Assembly in Real-Time. J. Vis Exp. 30 (2009) 1432, 3 pages.
Biju et al., Delivering quantum dots to cells: bioconjugated quantum dots for targeted and nonspecific extracellular and intracellular imaging. Chem. Soc. Rev. 39 (2010) 3031-3056.
Algar and Krull. Toward a Multiplexed Solid-Phase Nucleic Acid Hybridization Assay Using Quantum Dots as Donors in Fluorescence Resonance Energy Transfer. Anal Chem. 81 (2009) 4113-4120.
Gao et al. In vivo cancer targeting and imaging with semiconductor quantum dots. Nature Biotechnology 22 (2004) 969-976.
Gussin et al. Binding of Muscimol-Conjugated Quantum Dots to GabaC Receptors. J. Am Chem. Soc. 128 (2006)15701-15713.
He et al. Highly Luminescent Water-Dispersible Silicon Nanowires for Long Term Immunofluorescent Cellular Imaging. Angew. Chem. Int. Ed. 50 (2011) 3080-3083.
Heiss et al. Image-guided convection-enhanced delivery of muscimol to the primate brain. J Neurosurg. 112 (2010) 790-795.
Lugo et al. Remote switching of cellular activity and cell signaling using light in conjunction with quantum dots. Biomedical Optics Express 3. (2012) 447-454.
Pappas et al. Nanoscale Engineering of a Cellular Interface with Semiconductor Nanoparticle Films for Photoelectric Stimulation of Neurons. Nano Letters 7 (2007) 513-519.
Rosenthal et al. Biocompatible Quantum Dots for Biological Applications. Chem Biol. 18 (2011) 10-24.
Templeton. Tiny Q-dots may enable more precise brain surgery. Pittsburgh Post-Gazette, Apr. 10, 2007, 4 pages.
van Rooy et al. Comparison of five different targeting ligands to enhance accumulation of liposomes into the brain. Journal of Controlled Release 150 (2011) 30-36.
Wen et al. Theranostic liposomes loaded with quantum dots and apomorphine for brain targeting and bioimaging. International Journal of Nanomedicine 7 (2012) 1599-1611.
Zhong et al. Modular design of an ultrahigh-intensity nanoparticle probe for cancer cell imaging and rapid visual detection of nucleic acids. Chem Commun., 48 (2012) 6277-6279.
Baker and Baker. Luminescent Carbon Nanodots: Emergent Nanolights. Angew. Chem. Int. Ed. 49 (2010) 6726-6744.
Hofmann-Amtenbrink et al. Superparamagnetic nanoparticles for biomedical applications, Nanostructured Materials for Biomedical Applications, (ed. M.C. Tan.) 2009, chap. 5, 119-149.
Joeres et al. Quantitative Comparison of Optical Coherence Tomography after Pegaptanib or Bevacizumab in Neovascular Age-Related Macular Degeneration, Ophthalmology 115 (2008) 347-354.
Taylor et al., "Glycogen Synthase Kinase 3 Inactivation Drives T-bet-Mediated Downregulation of Co-receptor PD-1 to Enhance CD8+ Cytolytic T Cell Responses," Immunity, Feb. 16, 2016, vol. 44, No. 2, pp. 274-286.
Husseini el al., "Ultrasonic-Activated Micellar Drug Delivery for Cancer Treatment," J Pharm Sci, May 27, 2008, vol. 98, No. 3, pp. 795-811.
Kong et al., "Efficacy of Liposomes and Hyperthermia in a Human Tumor Xenograft Model: Importance of Triggered Drug Release," Cancer Research, Dec. 15, 2000, vol. 60, pp. 6950-6957.
Phenix et al., "High Intensity Focused Ultrasound Technology, Its Scope and Applications in Therapy and Drug Delivery," Journal of Pharmacy & Pharmaceutical Sciences, Mar. 31, 2014, vol. 17, No. 1, pp. 136-153.
PCT Form 210, International Search Report for PCT/US2018/054880, dated Jan. 9, 2019.
PCT Form 237, Written Opinion of the International Searching Authority for PCT/US2018/054880, dated Jan. 9, 2019.

\* cited by examiner

EARLY CANCER DETECTION AND ENHANCED IMMUNOTHERAPY

This patent application claims priority to U.S. Provisional Patent Application No. 62/569,592, entitled "Cancer Treatment Methods Using Thermotherapy and/or Enhanced Immunotherapy", filed on Oct. 8, 2017, and to U.S. Provisional Patent Application No. 62/577,485, entitled "Cancer Treatment Methods Using Thermotherapy and/or Enhanced Immunotherapy", filed on Oct. 26, 2017, and is a continuation-in-part of application Ser. No. 15/143,981, entitled "Early Cancer Detection And Enhanced Immunotherapy", filed May 2, 2016, which is a continuation-in-part of application Ser. No. 14/976,321, entitled "Method to Visualize Very Early Stage Neoplasm or Other Lesions", filed Dec. 21, 2015, the disclosure of each of which is hereby incorporated by reference as if set forth in their entirety herein.

Various factors may lead one to suspect the presence of a small cancerous or neoplastic tumor in a patient. Such factors include the patient's genetic history, environmental conditions to which the patient is or has been exposed, the presence of biomarkers in the patient's blood, or the presence of a lesion on a patient's skin or mucosal surface. A small neoplasm of 1 to 2 millimeters (mm) in diameter, however, is often not recognized unless and until it produces some clinical symptom.

In a patient having a genetic mutation indicating a predisposition to cancer, prophylactic surgical intervention, such as a bilateral mastectomy performed in a patient having a genetic mutation indicating a predisposition to breast cancer, is seldom performed. Additionally, a genetic predisposition to one type of cancer may not lead to that type of cancer, e.g. breast cancer, but it may lead to another unsuspected type of cancer, e.g. malignant melanoma. Even if the other type of cancer is suspected, because of the finding of biomarkers in the blood, a small internal lesion may not be seen on radiography, or may not be accessible by surgery, or the collateral complications may not be acceptable. It may not suffice to just know the biomarker for a tumor, because this information may not indicate whether the tumor is a primary site or a metastatic site, the tissue of its origin, and/or its location. It is appreciated that some treatment techniques such as surgery or radiation may be useful, but only if the tumor is tissue specific. Radiation and chemotherapy also have their own side effects, and may not destroy the tumor completely. Larger tumors present a much complex problem, e.g., mutations in one area of the tumor are usually different from mutations in another area of the same tumor.

It is clearly preferable, then, to manage small early neoplasms that have not progressed to a larger tumor to provide the patient an improved clinical prognosis.

The invention includes a method of therapy for a non-surgically accessible tumor by administering a combination of thermotherapy and immunotherapy combined with gene delivery. The combination therapy beneficially treats the tumor and prevents tumor recurrence, either locally or at a different site, by boosting the patient's immune response both at the time or original therapy and/or for later therapy as a "booster" vaccine with or without viral-like particles (VLP) to the original therapy by administering them with checkpoint inhibitors, such as PD-1, PD-L1, CTLA-4, Jagged 1 inhibitor 15D11, etc. and anti-inflammatory agents, such as Rock inhibitors, such as Fasudil etc., Wnt inhibitors, such as niclosamide etc. to enhance cellular immune response of the patient while reducing the inflammatory response and preventing an auto immune reaction or cytokine storm. In one embodiment, the vaccine with or without VLP is combined with checkpoint inhibitors, such as PD-1, PD-L1, CTLA-4, Jagged 1 inhibitor 15D11, etc. and anti-inflammatory agents, Rock inhibitors, such as Fasudil or Botox, or Wnt inhibitor, such as niclosamide, ivermectin, etc. can be injected every six months or once a year, or is used in the treatment of recurrent metastatic disease. In another embodiment the antibody coated nanoparticles are coated with thermosensitive polymers which are released at the temperature or 41-42 C under thermotherapy and administered with checkpoint inhibitors, such as PD-1, PD-L1, CTLA-4, Jagged 1 inhibitor 15D11, etc. and Rocks inhibitors, such as Fasudil or Botox, or Wnt inhibitor, such as niclosamide or ivermectin, and an antineoplastic medication depending on the cancer, at lower dose than is normally recommended, but is made more effective by thermotherapy.

With respect to gene delivery, the inventive method may be used in cancer therapy, but is not limited to such use; it will be appreciated that the inventive method may be used for gene delivery in general. For example, the inventive method facilitates cellular gene uptake by current methods that lack a thermal energy component, such as electroporation, quantum dot delivery, etc. The controlled and precise application of thermal energy enhances gene and medication transfer to any cell, whether the cell is a neoplastic cell, a pre-neoplastic cell, or a normal cell.

The inventive method provides in vitro and in vivo precision immunotherapy to decrease or eradicate a malignant neoplasm at an early stage of the disease. This method provides a vaccination effect periodically to prevent at least the same kind of cancer or to treat recurrences.

One embodiment is a method for evaluating treatment outcome in a patient having a genetic predisposition for a malignant neoplasm before clinical manifestation of the neoplasm can be seen radiographically. The method permits visualization of any tumor, whether located externally on a patient's body or located internally in the body, and as small as 2 mm in diameter, producing a biomarker, either a biomarker specific for the tumor or a general biomarker.

In general, a biomarker indicates a disease process. As subsequently described, a biomarker can be a protein, antigen, enzyme, hormone, carbohydrate, toxin, DNA, an organism such as bacteria, tumor cell, exosome, or indirectly an antibody, present in a liquid biopsy specimen. It can be produced by the plasma cells, against a tumor antigen, etc.

The method uses antibodies conjugated with nanoparticles which include but are not limited to quantum dots, with the conjugated form collectively termed functionalized nanoparticles, that are heated under specified conditions to produce a photoacoustic or thermoacoustic signal that is then recorded and visualized to locate the tumor to which the nanoparticles are attached. Nanoparticles may be used for qualitative and quantitative assessment of an analyte in the blood or other tissue using photoacoustic/thermoacoustic technology, U.S. Pat. No. 8,554,296. As previously stated, as used herein, unless specifically stated otherwise, nanoparticles include but are not limited to quantum dots.

Early stage small neoplastic cells produce biomarkers that are either specific to the tumor cells or that represent the body's response to the tumor as an antibody. The biomarkers can be proteomic, genetic, epigenetic or glycomic biomolecules. These biomolecules can be recognized in the patient's tissue samples or in the blood or fluids. Their existence can be demonstrated thus far chemically using, e.g., immunoassay or PCR methods. Quantitation of these biomarkers is also important to determine disease progression and prognosis of the disease.

Biomarkers for many diseases are found in the blood. As subsequently disclosed, biomarkers detected in a liquid biopsy sample are used to generate antibodies against them using known methods in the art. The anti-tumor antibodies are used to coat nanoparticles in the inventive method, where a lesion can be imaged regardless of the lesion size or location in the body. The method is not limited to tumor detection and/or therapy. As only one example, detecting an antibody against anti-beta-amyloid protein present in Alzheimer's disease in a liquid biopsy specimen, the method renders the plaque visible with the nanoparticles and accessible to the inventive treatment. As another example, the method can also be used to detect and/or treat inflammatory processes, etc.

The inventive method is applicable to any processes or diseases that produce a biomarker detectable in a liquid biopsy specimen. It is applicable to a lesion including an abscess, an ulcer, a tumor either benign or malignant, an ischemic area of a stroke and/or an area of the brain affected by a stroke whether visible or microscopically.

Well over a thousand proteins are differentially expressed in human cancers and thus may serve as biomarkers. Such proteins play a role in cancer-related processes such as angiogenesis, apoptosis, cell differentiation, cell signaling, hematopoiesis, hormonal control, immune reactions, etc. Exemplary biomarkers include, but are not limited to, CEA for both malignant pleural effusion and peritoneal cancer dissemination; HER-2/neu for stage IV breast cancer; bladder tumor antigen for urothelial cell carcinoma; thyroglobulin for thyroid cancer metastasis; α-fetoprotein for hepatocellular carcinoma; PSA for prostate cancer; CA 125 for non-small cell lung cancer; CA 19.9 for pancreatic cancer; CA 15.3 for breast cancer; the combination of leptin, prolactin, osteopontin, and IGF-II for ovarian cancer; the combination of CD98, fascin, sPIgR, and 14-3-3 eta for lung cancer; troponin I for myocardial infarction, and B-type natriuretic peptide for congestive heart failure. While the previous nine proteins are the only approved markers for cancer testing to date, they are but a small fraction of the total number of available biomarkers, and their sensitivity and specific vary.

Other common biomarkers include the estrogen receptor/progesterone receptor (ER/PR), HER-2/neu, and ESFR for breast cancer, and TIMP-1-associated with serum HER2-positive breast cancer; KRAS and UGT1A1 for colorectal cancer; HER-2/neu for gastric cancer, c-KIT, CD20 antigen, CD30, and FIP1L1-PDGRF alpha, and PDGFR for GIST; Philadelphia Chromosome (BCR/ABL)/PML/RAR alpha and TPMT/UGT1A1/ALK EGFR for leukemia/lymphoma; KRAS/EGFR for lung cancer, and BRAF and S100 for melanoma.

Other examples of biomarkers include tumor suppressors that are lost in cancers, such as BRCA1, BRCA2; RNA such as mRNA, microRNA; proteins found in body fluids or tissue such as prostate specific antigen and CA-125; gene and protein based biomarkers; and nonspecific biomarkers such as glycosaminoglycans in body fluids; alkaline phosphatase and urinary hydroxyproline in skeletal involvement; hyaluronic acid excretion and urinary hydroxyproline in bone disease, and combinations thereof.

In malignancies, the biomarkers may be released into the circulation either prior to or after the tumor has grown sufficiently to become metastatic. Small tumors (less than about 2 mm) seldom have any clinical manifestations, however even such small tumors can release chemical and/or biomarkers into the circulation.

The existence of biomarkers in the circulation has been known, but has not met the threshold for locating tumor cells that could not be imaged radiographically or by ultrasound as long as the tumors were asymptomatic. Available imaging methods such as x-ray, magnetic resonance imaging (MRI), functional MRI, computed tomography (CT) scans, CT ultrasound, etc. may not permit visualization of lesions smaller than about 3 mm in diameter. This has been the case for most malignant tumors, or when a malignant tumor is created from a benign precursor lesion such as nevus, breast unspecific cyst or unspecific scar, prostate tumors along with benign prostate hypertrophy, or uterus cancer inside the uterus fibroma, melanoma inside a skin nevus or choroidal nevus under the retina in the eye or in a seborrheic keratosis, etc. Moreover, it is often difficult to follow a cancerous tumor which has been irradiated but may still harbor malignant cells, and that can start growing with time and metastasize before it shows a local growth that is detected by conventional imaging or other methods.

The diagnosis of a malignant tumor may be extremely difficult, even when a tumor is visible clinically or radiologically, e.g. a uterus fibroma that may have some malignant transformation. Moreover, a diagnosis also affects the decision whether or not and also how to remove the tumor. As one example, accessing the uterus through a small incision, and removing the tumor piece by piece using an endoscope and a cutting probe, has a fast post-operative recovery. Such a method is in contrast to completely removing the uterus with the tumor intact out of caution that the tumor may harbor neoplastic cells, but using a large incision with significantly higher operative risks and post-operative complication probabilities. Another, more problematic example, is the decision for a woman having genetic disposition to breast cancer without any physical or radiological manifestation. The woman must endure the stress and fear not knowing if or when she may develop breast cancer, and must consider prophylactic removal of both breasts. As another example, a personal decision whether or not to undergo radiation therapy when a nevus is discovered under the retina, and biopsy results that often do not provide definitive information because of the diversity of the cells in the entire area of the tumor.

When the tumor site is unknown, locating a biomarker in the circulation may be akin to finding a needle in a hay stack. For any particular tumor or cancer, not all biomarkers are even known. Similarly, finding a micro DNA in the circulation may not provide an answer when the tumor is either invisible or has already metastasized. An example of this occurs in patients with uveal melanomas, having a mortality rate of about 50%, even if the tumors undergoes radiation, at the time the ophthalmologist discovers the tumor. This points to the fact that a malignant tumor can metastasize very early, at times even when the size of the tumor is about 2 mm in diameter which is equal to about one million cells. In general, these lesions do not have any symptoms.

The inventive method makes it possible to evaluate a patient with genetic predisposition of a malignant neoplasm before its clinical manifestation can be seen radiographically.

In one embodiment, the presence of one or more biomarkers is evaluated in any body fluid or organ. Exemplary bodily fluids include, but are not limited to, urine, blood, cerebrospinal fluid (CSF), eye cavity fluid, tear film, sputum, fluid obtained from the trachea, bronchi, abdominal cavity, vagina, uterus etc. The biomarkers are analyzed in vitro by methods known in the art, e.g., immunoassays including enzyme-linked immunoassay (ELISA), Western blots, fluorescence in situ hybridization (FISH), polymerase chain reaction (PCR), etc. The biomarkers are then conjugated with functionalized antibody coated nanoparticles and/or quantum dots, as known in the art.

In one embodiment one obtains a liquid biopsy sample. Such a sample may be obtained from, e.g., blood, urine, cerebrospinal fluid (CFS), aqueous or vitreous or abdominal cavity fluid, lymph node fluid, bladder fluid, milk duct fluid, sputum, gastric fluid, bile duct fluid, sinus fluid, etc. The patient may or may not have any clinical symptom. The patient may or may not have history of a family disposition for tumors in and/or cancer of the breast, brain, lung, prostate, ovary, pancreas, etc., or a genetic abnormality leading to progression in diseases such as, e.g., Alzheimer's, Parkinson's, post traumatic brain syndrome, brain tumor, other neurological disease, age related macular degeneration, an infectious disease, an immune response, etc. The method evaluates the components of the sample for cell free nucleic acid-based biomarkers including but not limited to micoRNA and microDNA; protein-based biomarkers, extracellular vesicle (EV)-based biomarkers that are contained within exosomes, extracellular vesicles, or microvesicles, and circulating tumor cell (CTC)-based biomarkers. The method uses methodologies such as next generation sequencing (NGS) or recombinant affinity reagents fabricated into nanostructures such as carbon nanotubes, nanowires, quantum dots, or gold nanoshells, to enhance their detection with the use of, e.g., surface-enhanced Raman scattering (SERS), as known in the art.

For example, if a known tumor exists and there is a known biomarker for the tumor, one may have or prepare an antibody against the tumor to be used in both imaging and therapy. Large tumors with symptoms can be imaged, but before the inventive method, there was a problem when a biomarker was present in a liquid biopsy specimen but the tumor was invisible, e.g., an early stage of a tumor, and there was no symptomatic or radiographic evidence of the tumor.

Detecting a tumor biomarker, typically a protein or a glycoprotein, in a liquid biopsy specimen is facilitated by the inventive method. Once detected, an antibody against that tumor biomarker can be prepared. The antitumor biomarker antibody is used to located the tumor. Antibody production is a well-known method in the art, and it will be appreciated that the antibody against either or both of the tumor biomarker and the tumor cell may be recombinant, monoclonal, polyclonal, or an aptamer. The prepared antitumor cell antibodies are conjugated with nanoparticles and administered to a patient, where they target the tumor cells and can be detected and/or treated. Detection is by photoacoustic/thermoacoustic imaging technology. Treatment is at least by one of thermal energy. The photoacoustic detection and thermal treatment is described herein.

In one embodiment, any specific tumor related biomarker may be used. One example uses trastuzumab or herceptin, a recombinant monoclonal antibody, against the oncogene HER-2, previously mentioned, which is a member of the human epidermal growth factor receptor (HER/EGFR/ERBB) family. Other examples of known monoclonal antibodies or biologics include, but are not limited to, rituximab, cetuximab, racotunomab, obinotuzumab, pertuzumab, belaniatumomab, bevacizumab, nivolumab, ofatumumab, botezomib, daratumumab, ipilumumab, pembrolizumab, and daratumumab.

In one embodiment, in the absence of a specific biomarker, antibodies against biomarkers that are shared by a number of the tumors may be used. Such biomarkers include glycosaminoglycan, which is specific for a group of cancers such as bladder, gastrointestinal, glioblastoma, etc. Antibodies against such biomarkers are then conjugated with nanoparticles, termed functionalized nanoparticles. The term "functionalized" indicates nanoparticles that have been coated to render them soluble, biocompatible, and/or targeted by conjugating them with a biomolecule such as an antibody.

In one embodiment, the pluralities of nanoparticles may be one or more of the following compounds or contain one or more of the following components: quantum dots, nanowires, nanotubes, nanoshells, nanocages, perovskites, nanoparticles that are magnetic such as iron or iron oxide, paramagnetic, or nanoparticles that are non-magnetic such as gold, gold-silica, gold-iron, silica coated gold nanospheres and nanorods, ferritic, quartz, graphene, carbon, zinc oxide, piezoelectric, etc. Any of these nanoparticles, alone or in combination, may be conjugated or otherwise associated with the biomarkers' antibodies, using methods known in the art.

In another embodiment, self-assembling bio/nano hybrid material consisting of two constituents at the nanometer or molecular level composed of inorganic and organic compounds, having amphiphilic characteristics, i.e., hydrophilic and lipophilic components or micelles, which may be radioactive (e.g., $Cu^{64}$) or radioactive (e.g., tin) are prepared with biocompatible coatings and administered in the body for both therapy and imaging.

In one embodiment, the functionalized nanoparticles travel in the body and attach to receptors of desired cells, e.g., tumors, Alzheimer's plaque, drusen of the retina, etc. These nanoparticles are imaged by applying external thermal energy and/or by applying an electromagnetic radiation, microwave, radiofrequency waves or a reversible or alternating magnetic field. The thermal energy causes the nanoparticles to expand, producing an ultrasound wave in the tissue known as photoacoustic or thermoacoustic sound. The ultrasound wave can be detected by an ultrasonic receiver which is imaged in two to three dimensional formats as a tomogram. In another embodiment the plaques in Alzheimer's disease, and the drusen in age related macular degeneration, are rendered visible using silica coated nanoparticles<2 nm in diameter administered with turmeric, glycosaminoglycan, amyloid antibody, or percolan, etc. and are quantified. In another embodiment, the nanoparticles are conjugated with thermosensitive polymers, such as chitosan, polylactic poly glycolic acid, acrylic derivatives, polycaprolactone, and are conjugated with are conjugated with antibodies, medications, sterols, antibiotics, antifungals, antibacterials, antiproliferative agents, medications interfering with the normal cell signaling processes, with stimulatory or inhibitory action such as Wnt inhibitors ivernectin or Rho kinase inhibitors known as Rock inhibitors (e.g., fasudil or Botox) or dyes, etc. that can be released from silica coated gold nanoparticles when coated with thermosensitive polymers, e.g., chitosan coated nanoparticles heated to 40° C.-42° C., to treat various diseases including bacteria, fungi, parasites, plaque, drusen, inflammation, tumors, etc. In another embodiment, the plaques and drusen can be quantified by imaging using light, MRI, photoacoustic/thermoacoustic technology imaging, etc.

In another embodiment, the functionalized anti-biomarker-conjugated nanoparticle, ranges in size from 1 nm to 900 nm. In another embodiment, the functionalized biomarker ranges in size from 1 nm to 8 nm, chosen to enhance their elimination through the kidney for facilitated clearance.

In one embodiment, the nanoparticles are rendered magnetic by coating with a thin film of iron oxide prior to their conjugation with biomarkers' antibodies.

In one embodiment, the nanoparticles are rendered more biocompatible by coating with a compound, including but not limited to the following: (poly)ethylene glycol, cell penetrating peptide (CPP), activating CPP (ACPP), biotin, streptavidin, etc., as known in the art, prior to their injection in the body.

Thermal energy in the form of electromagnetic radiation, ultrasound, or an alternating magnetic field is applied, under the control of a photoacoustic/thermoacoustic imaging system, to the organ suspected of potentially harboring an as yet invisible neoplasm. The thermal energy applied increases preferentially the temperature of the exposed nanoparticle, and creates (e.g. using a laser light) a photoacoustic sound from the superficial lesions and or using focused ultrasound, microwave, RF, or an alternating magnetic field to produce a thermoacoustic sound from deep in the tissue located lesions, and to image or create a tomogram of the accumulated heated nanoparticles/tumor. This image or tomogram represents a suspected neoplasm in that organ, and is compared to an image taken without the thermal application radiographically.

In one embodiment, one administers functionalized antibody-coated nanoparticles that, once attached to tumor cells, become visible with a photoacoustic/thermoacoustic imaging unit that corroborates with an image obtained or not seen with other technology such as ultrasound, MRI, PET, CT scan, etc. In one embodiment, the images obtained with other instruments are either overlapped using a processor or are taken simultaneously during photoacoustic/thermoacoustic imaging. In one embodiment, after administration of the antibody-coated nanoparticle, an MRI image is overlapped with the photoacoustic image and compared by a processor to verify the changes in the imaged area.

In one embodiment, the nanoparticles are incorporated in liposomes. In this embodiment, they may contain medications or a dye that, upon attainment of a specific tumor temperature, are released. The type of medication is not limited, and can include anti-bacterial, anti-viral, anti-fungal, antineoplastic, anti-inflammatory such as acetyl cycline, anti-beta-amyloid protein, other antibodies, non-steroidal anti-inflammatory drugs, Rock inhibitors, Botox, Wnt inhibitors niclosamide, ivernectin, preventing inflammation or tumor growth, checkpoint inhibitors, immune stimulating agents, VLPs, anti-VEGF agents, anti-aggregation agents such as sterols, etc.

In another embodiment, antibody-coated nanoparticles conjugated with thermosensitive polymers such as chitosan, carrying any medication including but not limited to sterol, squalamine, lanosterol, is administered to a patient having a neurologic pathology such as Alzheimer's disease, Parkinson's disease, or age related retinal drusen, etc. In this embodiment, administration is either intravenous or local in the cerebrospinal fluid or vitreous cavity, respectively, or at another local site. After controllably increasing the temperature of the functionalized nanoparticle to between 40° C.-43° C. by increased energy delivery through a delivery source, under the control of the photoacoustic imaging system and a processor, the temperature-sensitive coating polymers such as chitosan melts and release medications specific to the pathology. For example, a medication to dissolve amyloid plaques would be administered to a patient with Alzheimer's disease; a medication to remove retinal drusen would be administered to a patient with age related retinal disease, etc.

In one embodiment, the functionalized nanoparticle, e.g., a nanoshell, nanocage, etc., is combined with biodendrimers that are conjugated with biomarkers and monoclonal antibodies and/or genes, e.g., siRNA, mRNA, etc., for simultaneous visualization and therapy.

In another embodiment, after thermal imaging one increases the temperature of the functionalized nanoparticles. This is achieved by increased energy delivered by a thermal delivery source under the control of the photoacoustic/thermoacoustic imaging system connected to a processor. The energy delivery unit increases the temperature of the functionalized nanoparticles to 41° C.-43° C. to melt the temperature-sensitive coating polymers such as chitosan, liposomes, and release anticancer medications, Rock inhibitors (e.g., fasudil, exoenzyme or Y27632, Botox etc.), Wnt inhibitors (e.g., niclosamide, etc.) or inhibitory genes, siRNA, miRNA, or checkpoint inhibitors, or introduce missing genes, or add any other genes for gene editing from the thermosensitive coating of the nanoparticles along with a CRISPR complex to modify the genetic composition of the tumor cells, etc. In another embodiment, the temperature of the functionalized nanoparticles is increased, by the thermal delivery unit via a processor under the control of the photoacoustic/thermoacoustic imaging unit to image the temperature and control it to 45° C.-47° C., to 47° C., or to 50° C. to kill the suspected tumor to which the antibody-coated nanoparticles are attached and release tumor antigens in the circulation to attract and enhance a cellular immune response to a tumor.

In one embodiment, one synthetizes hybrid, very small (1 nm-8 nm) gold silica nanoparticles that have a dual function, the nanoparticles antibody coated for imaging, and having photovoltaic and magnetic properties, to release one or more gene(s) or medication(s) at certain temperatures, creating a photoacoustic/thermoacoustic signal after heating for imaging in the body or by laser or light stimulation in the eye for simultaneous imaging and therapy.

In one embodiment, using antibody coated quantum dots and light of a specific wavelength that is absorbed by the quantum dot and emits light of a different wavelength, one can render the moving tumor cells and extracellular vesicle visible attached to the quantum dots visible in the retinal or choroidal vessels, or vessels and tumors of the skin, or tumors located beneath the skin and their feeding vessels, by light absorbed by the quantum dots circulating in the vessels, as is done in fluorescence angiography with appropriate filters and camera.

In another embodiment, a gold quantum dot in a mesoporous silica shell or cage is coated with an antibody or a biomarker to any cell, e.g., neuronal or tumor cells, retinal drusen, Alzheimer plaques, etc. for delivering medication or gene to an organ, e.g., retina or brain.

In another embodiment, the extent of plaque or drusen, as an indicator of disease progression in the brain or eye, respectively, can be evaluated by conjugating nanoparticles with antibodies to glycosaminoglycan, heparin sulfate, glycosaminoglycan, and/or heparin sulfate proteoglycan, and injecting the composition into the circulation of the body or locally to adhere to plaques or drusen for diagnosis, quantitation, and/or therapy with antibodies and medication.

In another embodiment, the pluralities of antibody coated nanoparticles are used for simultaneous imaging and thermotherapy of very small tumors. The nanoparticles are heated to a temperature ranging from 41° C.-43° C., releasing anti-cancer medication, such as rock inhibitors, such as Botox, exoenzyme or Y27632, or Wnt inhibitors (e.g., niclosamide or ivermectin) precisely at the desired location, along with inhibitory siRNA, or modify a gene using the CRISPR/cas9 system or another CRISPR system, additionally releasing checkpoint inhibitors such as CTLA-4 or PD-1 or Jagged 1 along with tumoricidal vectors, etc.

In one embodiment, the pluralities of antibody coated nanoparticles are rendered radioactive by coating with alpha or beta radiators that are antibody specific or nonspecific biomarkers of the tumor. The nanoparticles can also be coated with heat sensitive polymers, including but not limited to chitosan, PEG, poly amino esters, etc.

In one embodiment, checkpoint inhibitors defined as immune system components that act as co-stimulatory or co-inhibitory molecules are released from the pluralities of antibody coated nanoparticles from thermosensitive coating of the nanoparticles at temperature of 41 to 43 degrees C. along with poisons such as bee or snake venom, or other toxic agents that damage tumor cell membranes, or genes that inhibit tumor growth, siRNA, siDNA, mi RNA, mDNA along with the CRISPR/cas 9 complex or variations of these may be used.

In one embodiment, the pluralities of antibody coated nanoparticles are coated with a specific or a nonspecific biomarker such as glycosaminoglycan and injected into the circulation, into a body fluid such as the lymphatic system or cerebrospinal fluid (CSF), or inside a body cavity. Examples of injection sites include, but are not limited to, eye, sinuses, abdominal cavity, bladder, uterus, etc. The nanoparticles may also be injected into the breast ducts, e.g., through the nipple, inside the brain, into the prostate or other organ, or may even be applied topically. The injected nanoparticles circulate and seek cells bearing a receptor to their antibody, or perhaps cells with specific receptors or biomolecules, and readily attach within minutes or hours.

In one embodiment, specific or non-specific biomarkers' antibodies are conjugated with nanoparticles and injected either into circulation or locally into a body cavity. The nanoparticles travel and seek cells bearing specific receptors or biomolecules, and attach within a few hours. The patient's body or organ is then scanned, with the thermal energy producing radiation or an alternating or reversible magnetic field, microwave radiation, a laser, radiofrequency (RF) waves or focused ultrasound to heat the nanoparticles. Using photoacoustic/thermoacoustic technology, the sound wave generated by the thermal expansion of the nanoparticle induced by absorption of the thermal energy is recorded. The sound wave signals may originate from any part of the body, or from a specific organ.

In one embodiment, an alternating magnetic field produces heat in magnetic nanoparticles as a result of rapid circular or semicircular motion of the magnetic or paramagnetic nanoparticles heating them. The patient's body is scanned within the reversible magnetic field, and the photoacoustic sound is recorded as a temperature profile of the site of the nanoparticle/cell membrane imaged and location of the lesion is verified.

In another embodiment, other sources of thermal energy are used. Such sources include, but are not limited to, electromagnetic radiation, visible light, invisible light, infrared radiation, microwaves, or radiofrequency waves, focused ultrasound (FUS), etc. The nanoparticles are heated from body temperature of 37° C. to 40° C. or 43° C., or if needed to 45° C. At the desired temperature, e.g., 41° C.-43° C., the heat sensitive coating of the nanoparticle melts, releasing its cargo of, e.g., medication, gene, etc., thus facilitating or enhancing passage of these compounds through the membrane of the neoplastic cells.

In another embodiment, use of a photoacoustic technology unit controls the thermal delivery unit and the thermal energy delivered to the nanoparticles to maintain or reach a predetermined temperature for a desired time.

In one embodiment, the temperatures rise of the nanoparticles expands them, producing a photoacoustic or thermoacoustic sound wave. This sound wave is recorded by one or multiple ultrasonic receivers located on the patient's skin. The signal can be obtained from any part of the body, or from a specific organ, since the signal travels through the body as a wave. The signal or sound pulse is converted to an electric pulse in the receiver, then using a processor, is amplified and imaged on a monitor. A processor produces a two- or three-dimension image of the lesion, localizing the location of the sound and indicating the size of a lesion and its temperature by the amplitude of the sound pulse.

In one embodiment, photoacoustic imaging is used for a very early stage diagnosis of cancerous lesion that are less than 2 mm in diameter, which are radiographically invisible without knowing their exact location in the body.

In one embodiment using photoacoustic technology and a specific or non-specific tumor biomarker, a very small lesion (<2 mm in diameter) is imaged in the body when the tumor has not caused any clinical symptom. The inventive method thus is used to differentiate a malignant lesion from a benign lesion, even if the cancerous lesion is inside a begin lesion. It is noteworthy that biopsy of these very small tumors, even when the lesion is visible, e.g., on skin or under the retina, may not yield malignant cells if the biopsy is performed on a part of the lesion that contains benign cells. With tumors in the brain, it is most often the case that the tumors will not be noted absent a neurological symptom.

In one embodiment, the inventive method is used with specific biomarkers of a tumor such as breast cancer, prostate cancer, glioma, pancreatic malignancies, along with nonspecific biomarkers. The location and size of a malignant tumor in any organ is imaged in a patient with a genetic propensity to develop a tumor. The thermal energy may also be applied, if desired, to treat the lesion simultaneously with providing the photoacoustic effect. Subsequent evaluation of the level of these biomarkers in the blood indicate if the lesion was damaged or eliminated by the thermal energy increasing the biomarkers in the blood, including use of medicaments/dye released from the thermosensitive nanoparticle coating and/or other treatment agents delivered by the method as cargo in the nanoparticles.

In one embodiment, a combination of biomarkers can be used in an early stage. For example, specific or nonspecific bio-markers such as glycosaminoglycans can be used in imaging a malignant lesion using antibody-coated nanoparticles to photoacoustically image the presence of a very small early stage tumor anywhere in the body.

In another embodiment, the inventive method is employed to determine residual tumor cells that may have left at the site of a tumor resection or elsewhere in the body, and to treat or eliminate the residual tumor cells.

In another embodiment, the functionalized nanoparticles are conjugated with one of the recombinant, monoclonal, or polyclonal antibodies or aptamers known in the art and administered along with either one or more toxin(s) or antibodies, along with a medication that is provided at a much lower dose systemically to kill the already compromised tumor cells. Monoclonal antibodies that may be used include, but are not limited to, those shown in Table 1, e.g., rituximab, obinuzumab, oftumumab, etc.

TABLE 1

| Name | Trade name | Type | Source | Target | Use |
|---|---|---|---|---|---|
| 3F8 | | mab | mouse | GD2 | neuroblastoma |
| 8H9 | | mab | mouse | B7-H3 | neuroblastoma, sarcoma, metastatic brain cancers |
| Abagovomab | | mab | mouse | CA-125 (imitation) | ovarian cancer |
| Abciximab | ReoPro | Fab | chimeric | CD41 (integrin alpha-IIb) | platelet aggregation inhibitor |
| Abituzumab | | mab | humanized | CD51 | cancer |
| Abrilumab | | mab | human | integrin α4β7 | inflammatory bowel disease, ulcerative colitis, Crohn's disease |
| Actoxumab | | mab | human | *Clostridium difficile* | *Clostridium difficile* infection |
| Adalimumab | Humira | mab | human | TNF-α | Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| Adecatumumab | | mab | human | EpCAM | prostate and breast cancer |
| Aducanumab | | mab | human | beta-amyloid | Alzheimer's disease |
| Afelimomab | | F(ab')₂ | mouse | TNF-α | sepsis |
| Afutuzumab | | mab | humanized | CD20 | lymphoma |
| Alacizumab pegol | | F(ab')₂ | humanized | VEGFR2 | cancer |
| ALD518 | | ? | humanized | IL-6 | rheumatoid arthritis |
| Alemtuzumab | Campath, MabCampath | mab | humanized | CD52 | Multiple sclerosis |
| Alirocumab | | mab | human | NARP-1 | hypercholesterolemia |
| Altumomab pentetate | Hybri-ceaker | mab | mouse | CEA | colorectal cancer (diagnosis) |
| Amatuximab | | mab | chimeric | mesothelin | cancer |
| Anatumomab mafenatox | | Fab | mouse | TAG-72 | non-small cell lung carcinoma |
| Anetumab ravtansine | | mab | human | MSLN | cancer |
| Anifrolumab | | mab | human | interferon α/β receptor | systemic lupus erythematosus |
| Anrukinzumab (= IMA-638) | | mab | humanized | IL-13 | ? |
| Apolizumab | | mab | humanized | HLA-DR ? | hematological cancers |
| Arcitumomab | CEA-Scan | Fab' | mouse | CEA | gastrointestinal cancers (diagnosis) |
| Ascrinvacumab | | mab | human | activin receptor-like kinase 1 | cancer |
| Aselizumab | | mab | humanized | L-selectin (CD62L) | severely injured patients |
| Atezolizumab | | mab | humanized | CD274 | cancer |
| Atinumab | | mab | human | RTN4 | ? |
| Atlizumab (= tocilizumab) | Actemra, RoActemra | mab | humanized | IL-6 receptor | rheumatoid arthritis |
| Atorolimumab | | mab | human | Rhesus factor | hemolytic disease of the newborn[citation needed] |
| Bapineuzumab | | mab | humanized | beta amyloid | Alzheimer's disease |
| Basiliximab | Simulect | mab | chimeric | CD25 (α chain of IL-2 receptor) | prevention of organ transplant rejections |
| Bavituximab | | mab | chimeric | phosphatidylserine | cancer, viral infections |
| Bectumomab | LymphoScan | Fab' | mouse | CD22 | non-Hodgkin's lymphoma (detection) |
| Begelomab | | mab | mouse | DPP4 | ? |
| Belimumab | Benlysta, LymphoStat-B | mab | human | BAFF | non-Hodgkin lymphoma etc. |
| Benralizumab | | mab | humanized | CD125 | asthma |
| Bertilimumab | | mab | human | CCL11 (eotaxin-1) | severe allergic disorders |
| Besilesomab | Scintimun | mab | mouse | CEA-related antigen | inflammatory lesions and metastases (detection) |
| Bevacizumab | Avastin | mab | humanized | VEGF-A | metastatic cancer, retinopathy of prematurity |
| Bezlotoxumab | | mab | human | *Clostridium difficile* | *Clostridium difficile* infection |
| Biciromab | FibriScint | Fab' | mouse | fibrin II, beta chain | thromboembolism (diagnosis) |
| Bimagrumab | | mab | human | ACVR2B | myostatin inhibitor |
| Bimekizumab | | mab | humanized | IL17A and IL17F | ? |
| Bivatuzumab mertansine | | mab | humanized | CD44 v6 | squamous cell carcinoma |
| Blinatumomab | | BiTE | mouse | CD19 | cancer |
| Blosozumab | | mab | humanized | SOST | osteoporosis |

TABLE 1-continued

| Name | Trade name | Type | Source | Target | Use |
|---|---|---|---|---|---|
| Bococizumab | | mab | humanized | neural apoptosis-regulated proteinase 1 | dyslipidemia |
| Brentuximab vedotin | | mab | chimeric | CD30 (TNFRSF8) | hematologic cancers |
| Briakinumab | | mab | human | IL-12, IL-23 | psoriasis, rheumatoid arthritis, inflammatory bowel diseases, multiple sclerosis |
| Brodalumab | | mab | human | IL-17 | inflammatory diseases |
| Brolucizumab | | mab | humanized | VEGFA | ? |
| Brontictuzumab | | mab | | Notch 1 | cancer |
| Canakinumab | Ilaris | mab | human | IL-1? | rheumatoid arthritis |
| Cantuzumab mertansine | | mab | humanized | mucin CanAg | colorectal cancer etc. |
| Cantuzumab ravtansine | | mab | humanized | MUC1 | cancers |
| Caplacizumab | | mab | humanized | VWF | thrombotic thrombocytopenic purpura, thrombosis |
| Capromab pendetide | Prostascint | mab | mouse | prostatic carcinoma cells | prostate cancer (detection) |
| Carlumab | | mab | human | MCP-1 | oncology/immune indications |
| Catumaxomab | Removab | 3funct | rat/mouse hybrid | EpCAM, CD3 | ovarian cancer, malignant ascites, gastric cancer |
| cBR96-doxorubicin immunoconjugate | | mab | humanized | Lewis-Y antigen | cancer |
| Cedelizumab | | mab | humanized | CD4 | prevention of organ transplant rejections, treatment of autoimmune diseases |
| Certolizumab pegol | Cimzia | Fab | humanized | TNF-α | Crohn's disease |
| Cetuximab | Erbitux | mab | chimeric | EGFR | metastatic colorectal cancer and head and neck cancer |
| Ch.14.18 | | mab | chimeric | ??? | neuroblastoma |
| Citatuzumab bogatox | | Fab | humanized | EpCAM | ovarian cancer and other solid tumors |
| Cixutumumab | | mab | human | IGF-1 receptor | solid tumors |
| Clazakizumab | | mab | humanized | *Oryctolagus cuniculus* | rheumatoid arthritis |
| Cleno1iximab | | mab | chimeric | CD4 | rheumatoid arthritis |
| Clivatuzumab tetraxetan | hPAM4-Cide | mab | humanized | MUC1 | pancreatic cancer |
| Codrituzumab | | mab | humanized | glypican 3 | cancer |
| Coltuximab ravtansine | | mab | chimeric | CD19 | cancer |
| Conatumumab | | mab | human | TRAIL-R2 | cancer |
| Concizumab | | mab | humanized | TFPI | bleeding |
| Crenezumab | | mab | humanized | 1-40-β-amyloid | Alzheimer's disease |
| CR6261 | | mab | human | Influenza A hemagglutinin | infectious disease/influenza A |
| Dacetuzumab | | mab | humanized | CD40 | hematologic cancers |
| Daclizumab | Zenapax | mab | humanized | CD25 (α chain of IL-2 receptor) | prevention of organ transplant rejections |
| Dalotuzumab[39] | | mab | humanized | insulin-like growth factor I receptor | cancer etc. |
| Dapirolizumab pegol | | mab | humanized | CD40 ligand | ? |
| Daratumumab | | mab | human | CD38 (cyclic ADP ribose hydrolase) | cancer |
| Dectrekumab | | mab | human | IL-13 | ? |
| Demcizumab | | mab | humanized | DLL4 | cancer |
| Denintuzumab mafodotin | | mab | humanized | CD19 | cancer |
| Denosumab | Prolia | mab | human | RANKL | osteoporosis, bone metastases etc. |
| Derlotuximab biotin | | mab | chimeric | histone complex | recurrent glioblastoma multiforme |
| Detumomab | | mab | mouse | B-lymphoma cell | lymphoma |
| Dinutuximab | | mab | chimeric | ganglioside GD2 | neuroblastoma |
| Diridavumab | | mab | human | hemagglutinin | influenza A |
| Dorlimomab aritox | | F(ab')$_2$ | mouse | ? | ? |
| Drozitumab | | mab | human | DR5 | cancer etc. |
| Duligotumab | | mab | human | HER3 | ? |
| Dupilumab | | mab | human | IL4 | atopic diseases |
| Durvalumab | | mab | human | CD274 | cancer |
| Dusigitumab | | mab | human | ILGF2 | cancer |
| Ecromeximab | | mab | chimeric | GD3 ganglioside | malignant melanoma |
| Eculizumab | Soliris | mab | humanized | C5 | paroxysmal nocturnal hemoglobinuria |
| Edobacomab | | mab | mouse | endotoxin | sepsis caused by Gram-negative bacteria |
| Edrecolomab | Panorex | mab | mouse | EpCAM | colorectal carcinoma |

TABLE 1-continued

| Name | Trade name | Type | Source | Target | Use |
|---|---|---|---|---|---|
| Efalizumab | Raptiva | mab | humanized | LFA-1 (CD11a) | psoriasis (blocks T-cell migration) |
| Efungumab | Mycograb | scFv | human | Hsp90 | invasive *Candida* infection |
| Eldelumab | | mab | human | interferon gamma-induced protein | Crohn's disease, ulcerative colitis |
| Elgemtumab | | mab | human | ERBB3 | cancer |
| Elotuzumab | | mab | humanized | SLAMF7 | multiple myeloma |
| Elsilimomab | | mab | mouse | IL-6 | ? |
| Emactuzumab | | mab | humanized | CSF1R | cancer |
| Emibetuzumab | | mab | humanized | HHGFR | cancer |
| Enavatuzumab | | mab | humanized | TWEAK receptor | cancer etc. |
| Enfortumab vedotin | | mab | human | AGS-22M6 | cancer expressing Nectin-4 |
| Enlimomab pegol | | mab | mouse | ICAM-1 (CD54) | ? |
| Enoblituzumab | | mab | humanized | B7-H3 | cancer |
| Enokizumab | | mab | humanized | IL9 | asthma |
| Enoticumab | | mab | human | DLL4 | ? |
| Ensituximab | | mab | chimeric | 5AC | cancer |
| Epitumomab cituxetan | | mab | mouse | episialin | ? |
| Epratuzumab | | mab | humanized | CD22 | cancer, SLE |
| Erlizumab | | F(ab')$_2$ | humanized | ITGB2 (CD18) | heart attack, stroke, traumatic shock |
| Ertumaxomab | Rexomun | 3funct | rat/mouse hybrid | HER2/neu, CD3 | breast cancer etc. |
| Etaracizumab | Abegrin | mab | humanized | integrin αvβ3 | melanoma, prostate cancer, ovarian cancer etc. |
| Etrolizumab | | mab | humanized | integrin α7 β7 | inflammatory bowel disease |
| Evinacumab | | mab | human | angiopoietin 3 | dyslipidemia |
| Evolocumab | | mab | human | PCSK9 | hypercholesterolemia |
| Exbivirumab | | mab | human | hepatitis B surface antigen | hepatitis B |
| Fanolesomab | NeutroSpec | mab | mouse | CD15 | appendicitis (diagnosis) |
| Faralimomab | | mab | mouse | interferon receptor | ? |
| Farletuzumab | | mab | humanized | folate receptor 1 | ovarian cancer |
| Fasinumab | | mab | human | HNGF | acute sciatic pain |
| FBTA05 | Lymphomun | 3funct | rat/mouse hybrid | CD20 | chronic lymphocytic leukaemia |
| Felvizumab | | mab | humanized | respiratory syncytial virus | respiratory syncytial virus infection |
| Fezakinumab | | mab | human | IL-22 | rheumatoid arthritis, psoriasis |
| Ficlatuzumab | | mab | humanized | HGF | cancer etc. |
| Figitumumab | | mab | human | IGF-1 receptor | adrenocortical carcinoma, non-small cell lung carcinoma etc. |
| Firivumab | | mab | human | influenza A virus hemagglutinin | ? |
| Flanvotumab | | mab | human | TYRP1(glycoprotein 75) | melanoma |
| Fletikumab | | mab | human | IL 20 | rheumatoid arthritis |
| Fontolizumab | HuZAF | mab | humanized | IFN-γ | Crohn's disease etc. |
| Foralumab | | mab | human | CD3 epsilon | ? |
| Foravirumab | | mab | human | rabies virus glycoprotein | rabies (prophylaxis) |
| Fresolimumab | | mab | human | TGF-β | idiopathic pulmonary fibrosis, focal segmental glomerulosclerosis, cancer |
| Fulranumab | | mab | human | NGF | pain |
| Futuximab | | mab | chimeric | EGFR | ? |
| Galiximab | | mab | chimeric | CD80 | B-cell lymphoma |
| Ganitumab | | mab | human | IGF-I | cancer |
| Gantenerumab | | mab | human | beta amyloid | Alzheimer's disease |
| Gavilimomab | | mab | mouse | CD147 (basigin) | graft versus host disease |
| Gemtuzumab ozogamicin | Mylotarg | mab | humanized | CD33 | acute myelogenous leukemia |
| Gevokizumab | | mab | humanized | IL-1β | diabetes etc. |
| Girentuximab | Rencarex | mab | chimeric | carbonic anhydrase 9 (CA-IX) | clear cell renal cell carcinoma[81] |
| Glembatumumab vedotin | | mab | human | GPNMB | melanoma, breast cancer |
| Golimumab | Simponi | mab | human | TNF-α | rheumatoid arthritis, psoriatic arthritis, ankylosing spondylitis |
| Gomiliximab | | mab | chimeric | CD23 (IgE receptor) | allergic asthma |
| Guselkumab | | mab | human | IL23 | psoriasis |
| Ibalizumab | | mab | humanized | CD4 | HIV |

TABLE 1-continued

| Name | Trade name | Type | Source | Target | Use |
|---|---|---|---|---|---|
| Ibritumomab tiuxetan | Zevalin | mab | mouse | CD20 | non-Hodgkin's lymphoma |
| Icrucumab | | mab | human | VEGFR-1 | cancer etc. |
| Idarucizumab | | mab | humanized | dabigatran | reversal of anticoagulant effects of dabigatran |
| Igovomab | Indimacis-125 | F(ab')$_2$ | mouse | CA-125 | ovarian cancer (diagnosis) |
| IMAB362 | | mab | human | CLDN18.2 | gastrointestinal adenocarcinomas and pancreatic tumor |
| Imalumab | | mab | human | MIF | cancer |
| Imciromab | Myoscint | mab | mouse | cardiac myosin | cardiac imaging |
| Imgatuzumab | | mab | humanized | EGFR | cancer |
| Inclacumab | | mab | human | selectin P | ? |
| Indatuximab ravtansine | | mab | chimeric | SDC1 | cancer |
| Indusatumab vedotin | | mab | human | GUCY2C | cancer |
| Infliximab | Remicade | mab | chimeric | TNF-α | rheumatoid arthritis, ankylosing spondylitis, psoriatic arthritis, psoriasis, Crohn's disease, ulcerative colitis |
| Intetumumab | | mab | human | CD51 | solid tumors (prostate cancer, melanoma) |
| Inolimomab | | mab | mouse | CD25 (α chain of IL-2 receptor) | graft versus host disease |
| Inotuzumab ozogamicin | | mab | humanized | CD22 | cancer |
| Ipilimumab | Yervoy | mab | human | CD152 | melanoma |
| Iratumumab | | mab | human | CD30 (TNFRSF8) | Hodgkin's lymphoma |
| Isatuximab | | mab | chimeric | CD38 | cancer |
| Itolizumab | | mab | humanized | CD6 | ? |
| Ixekizumab | | mab | humanized | IL-17A | autoimmune diseases |
| Keliximab | | mab | chimeric | CD4 | chronic asthma |
| Labetuzumab | CEA-Cide | mab | humanized | CEA | colorectal cancer |
| Lambrolizumab | | mab | humanized | PDCD1 | antineoplastic agent |
| Lampalizumab | | mab | humanized | CFD | ? |
| Lebrikizumab | | mab | humanized | IL-13 | asthma |
| Lemalesomab | | mab | mouse | NCA-90 (granulocyte antigen) | diagnostic agent |
| Lenzilumab | | mab | human | CSF2 | ? |
| Lerdelimumab | | mab | human | TGF beta 2 | reduction of scarring after glaucoma surgery |
| Lexatumumab | | mab | human | TRAIL-R2 | cancer |
| Libivirumab | | mab | human | hepatitis B surface antigen | hepatitis B |
| Lifastuzumab vedotin | | mab | humanized | phosphate-sodium co-transporter | cancer |
| Ligelizumab | | mab | humanized | IGHE | severe asthma and chronic spontaneous urticarial |
| Lilotomab satetraxetan | | mab | mouse | CD37 | cancer |
| Lintuzumab | | mab | humanized | CD33 | cancer |
| Lirilumab | | mab | human | KIR2D | ? |
| Lodelcizumab | | mab | humanized | PCSK9 | hypercholesterolemia |
| Lokivetmab | | mab | veterinary | *Canis lupus familiaris* IL31 | ? |
| Lorvotuzumab mertansine | | mab | humanized | CD56 | cancer |
| Lucatumumab | | mab | human | CD40 | multiple myeloma, non-Hodgkin's lymphoma, Hodgkin's lymphoma |
| Lulizumab pegol | | mab | humanized | CD28 | autoimmune diseases |
| Lumiliximab | | mab | chimeric | CD23 (IgE receptor) | chronic lymphocytic leukemia |
| Lumretuzumab | | mab | humanized | ERBB3 | cancer |
| Mapatumumab | | mab | human | TRAIL-R1 | cancer |
| Margetuximab | | mab | humanized | ch4D5 | cancer |
| Maslimomab | | ? | mouse | T-cell receptor | ? |
| Mavrilimumab | | mab | human | GMCSF receptor α-chain | rheumatoid arthritis |
| Matuzumab | | mab | humanized | EGFR | colorectal, lung and stomach cancer |
| Mepolizumab | Bosatria | mab | humanized | IL-5 | asthma and white blood cell diseases |
| Metelimumab | | mab | human | TGF beta 1 | systemic scleroderma |
| Milatuzumab | | mab | humanized | CD74 | multiple myeloma and other hematological malignancies |

TABLE 1-continued

| Name | Trade name | Type | Source | Target | Use |
|---|---|---|---|---|---|
| Minretumomab | | mab | mouse | TAG-72 | tumor detection (and therapy?) |
| Mirvetuximab soravtansine | | mab | chimeric | folate receptor alpha | cancer |
| Mitumomab | | mab | mouse | GD3 ganglioside | small cell lung carcinoma |
| Mogamulizumab | | mab | humanized | CCR4 | cancer |
| Morolimumab | | mab | human | Rhesus factor | ? |
| Motavizumab | Numax | mab | humanized | respiratory syncytial virus | respiratory syncytial virus (prevention) |
| Moxetumomab pasudotox | | mab | mouse | CD22 | cancer |
| Muromonab-CD3 | Orthoclone OKT3 | mab | mouse | CD3 | prevention of organ transplant rejections |
| Nacolomab tafenatox | | Fab | mouse | C242 antigen | colorectal cancer |
| Namilumab | | mab | human | CSF2 | ? |
| Naptumomab estafenatox | | Fab | mouse | 5T4 | non-small cell lung carcinoma, renal cell carcinoma |
| Narnatumab | | mab | human | RON | cancer |
| Natalizumab | Tysabri | mab | humanized | integrin α4 | multiple sclerosis, Crohn's disease |
| Nebacumab | | mab | human | endotoxin | sepsis |
| Necitumumab | | mab | human | EGFR | non-small cell lung carcinoma |
| Nemolizumab | | mab | humanized | IL31RA | ? |
| Nerelimomab | | mab | mouse | TNF-α | ? |
| Nesvacumab | | mab | human | angiopoietin 2 | cancer |
| Nimotuzumab | Theracim, Theraloc | mab | humanized | EGFR | squamous cell carcinoma, head and neck cancer, nasopharyngeal cancer, glioma |
| Nivolumab | | mab | human | PD-1 | cancer |
| Nofetumomab merpentan | Verluma | Fab | mouse | ? | cancer (diagnosis) |
| Obiltoxaximab | | mab | chimeric | *Bacillus anthracis* anthrax | *Bacillus anthracis* spores |
| Obinutuzumab | Gazyva | mab | humanized | CD20 | Chronic lymphatic leukemia |
| Ocaratuzumab | | mab | humanized | CD20 | cancer |
| Ocrelizumab | | mab | humanized | CD20 | rheumatoid arthritis, lupus erythematosus etc. |
| Odulimomab | | mab | mouse | LFA-1 (CD11a) | prevention of organ transplant rejections, immunological diseases |
| Ofatumumab | Arzerra | mab | human | CD20 | chronic lymphocytic leukemia etc. |
| Olaratumab | | mab | human | PDGF-R α | cancer |
| Olokizumab | | mab | humanized | IL6 | ? |
| Omalizumab | Xolair | mab | humanized | IgE Fc region | allergic asthma |
| Onartuzumab | | mab | humanized | human scatter factor receptor kinase | cancer |
| Ontuxizumab | | mab | chimeric/humanized | TEM1 | cancer |
| Opicinumab[1] | | mab | human | LINGO-1 | multiple sclerosis |
| Oportuzumab monatox | | scFv | humanized | EpCAM | cancer |
| Oregovomab | OvaRex | mab | mouse | CA-125 | ovarian cancer |
| Orticumab | | mab | human | oxLDL | ? |
| Otelixizumab | | mab | chimeric/humanized | CD3 | diabetes mellitus type 1 |
| Otlertuzumab | | mab | humanized | CD37 | cancer |
| Oxelumab | | mab | human | OX-40 | asthma |
| Ozanezumab | | mab | humanized | NOGO-A | ALS and multiple sclerosis |
| Ozoralizumab | | mab | humanized | TNF-α | inflammation |
| Pagibaximab | | mab | chimeric | lipoteichoic acid | sepsis (*Staphylococcus*) |
| Palivizumab | Synagis, Abbosynagis | mab | humanized | F protein of respiratory syncytial virus | respiratory syncytial virus (prevention) |
| Panitumumab | Vectibix | mab | human | EGFR | colorectal cancer |
| Pankomab | | mab | humanized | tumor specific glycosylation of MUC1 | ovarian cancer |
| Panobacumab | | mab | human | *Pseudomonas aeruginosa* | *Pseudomonas aeruginosa* infection |
| Parsatuzumab | | mab | human | EGFL7 | cancer |
| Pascolizumab | | mab | humanized | IL-4 | asthma |
| Pasotuxizumab | | mab | chimeric/humanized | folate hydrolase | cancer |
| Pateclizumab | | mab | humanized | LTA | TNF |
| Patritumab | | mab | human | HER3 | cancer |
| Pembrolizumab | | mab | humanized | PDCD1 | cancer etc. |

TABLE 1-continued

| Name | Trade name | Type | Source | Target | Use |
|---|---|---|---|---|---|
| Pemtumomab | Theragyn | ? | mouse | MUC1 | cancer |
| Perakizumab | | mab | humanized | IL17A | arthritis |
| Pertuzumab | Omnitarg | mab | humanized | HER2/neu | cancer |
| Pexelizumab | | scFv | humanized | C5 | reduction of side effects of cardiac surgery |
| Pidilizumab | | mab | humanized | PD-1 | cancer and infectious diseases |
| Pinatuzumab vedotin | | mab | humanized | CD22 | cancer |
| Pintumomab | | mab | mouse | adenocarcinoma antigen | adenocarcinoma (imaging) |
| Placulumab | | mab | human | human TNF | ? |
| Polatuzumab vedotin | | mab | humanized | CD79B | cancer |
| Ponezumab | | mab | humanized | human beta-amyloid | Alzheimer's disease |
| Priliximab | | mab | chimeric | CD4 | Crohn's disease, multiple sclerosis |
| Pritoxaximab | | mab | chimeric | *E. coli* shiga toxin type-1 | ? |
| Pritumumab | | mab | human | vimentin | brain cancer |
| PRO 140 | | ? | humanized | CCR5 | HIV infection |
| Quilizumab | | mab | humanized | IGHE | asthma |
| Racotumomab | | mab | mouse | N-glycolylneuraminic acid | cancer |
| Radretumab | | mab | human | fibronectin extra domain-B | cancer |
| Rafivirumab | | mab | human | rabies virus glycoprotein | rabies (prophylaxis) |
| Ralpancizumab | | mab | humanized | neural apoptosis-regulated proteinase 1 | dyslipidemia |
| Ramucirumab | Cyramza | mab | human | VEGFR2 | solid tumors |
| Ranibizumab | Lucentis | Fab | humanized | VEGF-A | macular degeneration (wet form) |
| Raxibacumab | | mab | human | anthrax toxin, protective antigen | anthrax (prophylaxis and treatment) |
| Refanezumab | | mab | humanized | myelin-associated glycoprotein | recovery of motor function after stroke |
| Regavirumab | | mab | human | cytomegalovirus glycoprotein B | cytomegalovirus infection |
| Reslizumab | | mab | humanized | IL-5 | inflammations of the airways, skin and gastrointestinal tract |
| Rilotumumab | | mab | human | HGF | solid tumors |
| Rinucumab | | mab | human | platelet-derived growth factor receptor beta | neovascular age-related macular degeneration |
| Rituximab | MabThera, Rituxan | mab | chimeric | CD20 | lymphomas, leukemias, some autoimmune disorders |
| Robatumumab | | mab | human | IGF-1 receptor | cancer |
| Roledumab | | mab | human | RHD | ? |
| Romosozumab | | mab | humanized | sclerostin | osteoporosis |
| Rontalizumab | | mab | humanized | IFN-α | systemic lupus erythematosus |
| Rovelizumab | LeukArrest | mab | humanized | CD11, CD18 | haemorrhagic shock etc. |
| Ruplizumab | Antova | mab | humanized | CD154 (CD40L) | rheumatic diseases |
| Sacituzumab govitecan | | mab | humanized | tumor-associated calcium signal transducer 2 | cancer |
| Samalizumab | | mab | humanized | CD200 | cancer |
| Sarilumab | | mab | human | IL6 | rheumatoid arthritis, ankylosing spondylitis |
| Satumomab pendetide | | mab | mouse | TAG-72 | cancer (diagnosis) |
| Secukinumab | | mab | human | IL-17A | uveitis, rheumatoid arthritis psoriasis |
| Seribantumab | | mab | human | ERBB3 | cancer |
| Setoxaximab | | mab | chimeric | *E. coli* shiga toxin type-2 | ? |
| Sevirumab | | ? | human | cytomegalovirus | cytomegalovirus infection |
| Sibrotuzumab | | mab | humanized | FAP | cancer |
| SGN-CD19A | | mab | humanized | CD19 | acute lymphoblastic leukemia and B-cell non-Hodgkin lymphoma |
| SGN-CD33A | | mab | humanized | CD33 | Acute myeloid leukemia |
| Sifalimumab | | mab | humanized | IFN-α | SLE, dermatomyositis, polymyositis |
| Siltuximab | | mab | chimeric | IL-6 | cancer |
| Simtuzumab | | mab | humanized | LOXL2 | fibrosis |

TABLE 1-continued

| Name | Trade name | Type | Source | Target | Use |
|---|---|---|---|---|---|
| Siplizumab | | mab | humanized | CD2 | psoriasis, graft-versus-host disease (prevention) |
| Sirukumab | | mab | human | IL-6 | rheumatoid arthritis |
| Sofituzumab vedotin | | mab | humanized | CA 125 | ovarian cancer |
| Solanezumab | | mab | humanized | beta amyloid | Alzheimer's disease |
| Solitomab | | mab | mouse | EpCAM | ? |
| Sonepcizumab | | ? | humanized | sphingosine-1-phosphate | choroidal and retinal neovascularization |
| Sontuzumab | | mab | humanized | episialin | ? |
| Stamulumab | | mab | human | myostatin | muscular dystrophy |
| Sulesomab | LeukoScan | Fab | mouse | NCA-90 (granulocyte antigen) | osteomyelitis (imaging) |
| Suvizumab | | mab | humanized | HIV-1 | viral infections |
| Tabalumab | | mab | human | BAFF | B-cell cancers |
| Tacatuzumab tetraxetan | AFP-Cide | mab | humanized | alpha-fetoprotein | cancer |
| Tadocizumab | | Fab | humanized | integrin αIIbα | percutaneous coronary intervention |
| Talizumab | | mab | humanized | IgE | allergic reaction |
| Tanezumab | | mab | humanized | NGF | pain |
| Taplitumomab paptox | | mab | mouse | CD19 | cancer[citation needed] |
| Tarextumab | | mab | human | Notch receptor | cancer |
| Tefibazumab | Aurexis | mab | humanized | clumping factor A | *Staphylococcus aureus* infection |
| Telimomab aritox | | Fab | mouse | ? | ? |
| Tenatumomab | | mab | mouse | tenascin C | cancer |
| Teneliximab | | mab | chimeric | CD40 | ? |
| Teplizumab | | mab | humanized | CD3 | diabetes mellitus type 1 |
| Teprotumumab | | mab | human | CD221 | hematologic tumors |
| Tesidolumab | | mab | human | C5 | ? |
| TGN1412 | | ? | humanized | CD28 | chronic lymphocytic leukemia, rheumatoid arthritis |
| Ticilimumab (= tremelimumab) | | mab | human | CTLA-4 | cancer |
| Tildrakizumab | | mab | humanized | IL23 | immunologically mediated inflammatory disorders |
| Tigatuzumab | | mab | humanized | TRAIL-R2 | cancer |
| TNX-650 | | ? | humanized | IL-13 | Hodgkin's lymphoma |
| Tocilizumab[6](= atlizumab) | Actemra, RoActemra | mab | humanized | IL-6 receptor | rheumatoid arthritis |
| Toralizumab | mab | humanized | CD154 | (CD4OL) | rheumatoid arthritis, lupus nephritis etc. |
| Tosatoxumab | | mab | human | *Staphylococcus aureus* | ? |
| Tositumomab | Bexxar | ? | mouse | CD20 | follicular lymphoma |
| Tovetumab | | mab | human | CD140a | cancer |
| Tralokinumab | | mab | human | IL-13 | asthma etc. |
| Trastuzumab | Herceptin | mab | humanized | HER2/neu | breast cancer |
| TRBS07 | Ektomab | 3funct | ? | GD2 | melanoma |
| Tregalizumab | | mab | humanized | CD4 | ? |
| Tremelimumab | | mab | human | CTLA-4 | cancer |
| Trevogrumab | | mab | human | growth differentiation factor 8 | muscle atrophy due to orthopedic disuse and sarcopenia |
| Tucotuzumab celmoleukin | | mab | humanized | EpCAM | cancer |
| Tuvirumab | | ? | human | hepatitis B virus | chronic hepatitis B |
| Ublituximab | | mab | chimeric | MS4A1 | cancer |
| Ulocuplumab | | mab | human | C-X-C chemokine receptor type 4 | hematologic malignancies |
| Urelumab | | mab | human | 4-1BB | cancer etc. |
| Urtoxazumab | | mab | humanized | *Escherichia coli* | diarrhoea caused by *E. coli* |
| Ustekinumab | Stelara | mab | human | IL-12, IL-23 | multiple sclerosis, psoriasis, psoriatic arthritis |
| Vandortuzumab vedotin | | mab | humanized | STEAP1 | cancer |
| Vantictumab | | mab | human | Frizzled receptor | cancer |
| Vanucizumab | | mab | humanized | angiopoietin 2 | cancer |
| Vapaliximab | | mab | chimeric | AOC3 (VAP-1) | ? |
| Varlilumab | | mab | human | CD27 | ? |
| Vatelizumab | | mab | humanized | ITGA2 | ? |
| Vedolizumab | | mab | humanized | integrin α4β7 | Crohn's disease, ulcerative colitis |
| Veltuzumab | | mab | humanized | CD20 | non-Hodgkin's lymphoma |
| Vepalimomab | | mab | mouse | AOC3 (VAP-1) | inflammation |
| Vesencumab | | mab | human | NRP1 | ? |

TABLE 1-continued

| Name | Trade name | Type | Source | Target | Use |
|---|---|---|---|---|---|
| Visilizumab | Nuvion | mab | humanized | CD3 | Crohn's disease, ulcerative colitis |
| Volociximab | | mab | chimeric | integrin α5β1 | solid tumors |
| Vorsetuzumab mafodotin | | mab | humanized | CD70 | cancer |
| Votumumab | HumaSPECT | mab | human | tumor antigen CTAA16.88 | colorectal tumors |
| Zalutumumab | HuMax-EGFr | mab | human | EGFR | squamous cell carcinoma of the head and neck |
| Zanolimumab | HuMax-CD4 | mab | human | CD4 | rheumatoid arthritis, psoriasis, T-cell lymphoma |
| Zatuximab | | mab | chimeric | HER1 | cancer |
| Ziralimumab | | mab | human | CD147 (basigin) | ? |
| Zolimomab aritox | | mab | mouse | CD5 | systemic lupus erythematosus, graft-versus-host disease |

In another embodiment using photoacoustic/thermoacoustic technology, the circulating tumor, exosomes, or extracellular vesicles in the blood are quantified non-invasively by having a thermal energy source such as laser microwave, RF, or other unit mounted on the patient's wrist, neck, etc. and a receiver to count and record the sound wave generated by circulating cells to which the antibody-coated nanoparticles are attached.

In another embodiment, the ultrasonic receiver of the photoacoustic unit is an array of ultrasonic receivers mounted on a hand held probe. The hand held probe contacts the patient's skin via a gel placed over the area suspected to contain a tumor or lesion. It simultaneously records multiple photoacoustic signals from the lesion during thermal energy application. Thermal energy applied pulses can range from one per second to a million times or more per second. Each time a thermal pulse reaches the nanoparticles, the nanoparticles expand and create a photoacoustic/thermoacoustic response that is recorded by the photoacoustic receiver.

The probe can be moved in any direction, e.g., up and down, side to side, etc., over the skin while recording the sound waves from the nanoparticles. Using a processor in the photoacoustic/thermoacoustic unit, one uses the photoacoustic response data to construct a two- or three-dimensional image of the tumor. The hand held probe permits scanning any bodily surface, including but not limited to breast, eye, CNS, spinal cord, extremities, internal organs, eye, nose, chest, trachea, throat, abdomen, and urogenital organs. The data from the ultrasonic array probe of the photoacoustic/thermoacoustic unit is stored in a computer during the probe's motion, permitting video construction showing tumor shape, structure, location, etc. for video presentation, evaluation, and archiving.

In one embodiment, the unit is capable of storing vast quantities of data from photoacoustic signals. The unit is also capable of storing vast quantities of data from non-stationary tissues, e.g., circulating tumor cells and exosomes in blood vessels, that have accumulated antibody coated nanoparticles on their cell membranes. The targeted cells can also be any normal or abnormal circulating cell in the blood or lymphatic system. The photoacoustic unit reproduces signals from these mobile cells and/or exosomes as photoacoustic cinematography/angiography or video.

In one embodiment, the cinematography or video recording is done by the photoacoustic unit recording at least 30 frames/second of photoacoustic signals, and converting them into an image of a moving object. A cinematography or video is performed by obtaining at least 30 frames of photos of a moving object per second. In photoacoustic videography or photoacoustic angiography, 30 or more frames of pulse signals from the heated nanoparticles per second are needed to reproduce or convert the still images to a moving object, e.g., blood flow, etc. by the unit. Use of such a system is known: Peyman et al. Ophthalmic Surg Laser Imaging 43 (2012) 143-51 doi: 10.3928.15428877-20120105-01 showing, however, lower resolution because no nanoparticles or photoacoustic imaging system was employed, and expressly incorporated by reference herein in its entirety.

In one embodiment the photoacoustic processor converts the microscopic still images to a video or photoacoustic angiography; since the only moving parts in the vessels that are targeted with antibody coated nanoparticles are the circulating tumor cells or exosomes, extracellular vesicles or bubbles covered with antibody coated nanoparticles that are heated by a pulse of thermal energy produces an internal ultrasonic pulse signal recorded by the photoacoustic receiver. A moving image of the cells and exosomes can be created by the unit whether the cells are on the tumor interior or exterior.

Nanoparticle assisted photoacoustic video-angiography or nanoparticle assisted photoacoustic cinematography is novel and inventive. All "photoacoustic" terminology has previously been used for describing tissue heating or the difference in the temperature between two tissues, vessels vs. skin, and has been done with light alone, not in combination with nanoparticles. In one embodiment, the method is performed for therapy by providing the patient with at least one antibody-coated functionalized nanoparticle having a detectable property, with the antibody targeting the functionalized nanoparticle to a specific patient site, then heating the nanoparticles to generate a photoacoustic signal, i.e., thermal therapy, and imaging to visualize any localized nanoparticle at the site. The ultrasonic receiver of the photoacoustic unit is an array of ultrasonic receivers mounted on a hand held probe simultaneously recording multiple photoacoustic signals from the lesion during thermal energy application which in one embodiment is pulsating. The array of ultrasonic receivers of the photoacoustic unit mounted on a hand held probe simultaneously records multiple photoacoustic signals from the lesion or vessels during thermal energy application, reproducing motion of moving nanoparticles and/or cells as a nanoparticle assisted photoacoustic video-angiography or nanoparticle assisted photoacoustic cinematography.

In another embodiment, software associated with the photoacoustic/thermoacoustic unit can enhance either or both the photoacoustic signals and resulting images. Enhancement may facilitate differentiating exosomes from circulating cells due to the smaller exosome size. All exosomes or other types of extracellular vesicles are less than one micron; in contrast, tumor cells are five to twenty times larger than exosomes. The inventive system for the first time permits in vivo observation and separation of exosomes from tumor cells, and separation of circulating tumor cells from a tumor mass. The separated cells or cell structures can be observed, counted, and quantified to assess the therapeutic effect of a procedure on tumor cells.

In another embodiment, after imaging and therapy, the biomarkers are collected from liquid biopsies and compared with those obtained prior to therapy in different post-operative periods to confirm the therapeutic effect of the procedure and prognosticate the condition.

In another embodiment, the antibody coated nanoparticles are conjugated and administered with checkpoint inhibitors along with known immune therapy agents and vaccines to facilitate circulating killer cells attack and removal of tumor cells.

In another embodiment, the vaccines with or without VLP facilitate circulating killer cells attacking and removal of tumor cells, and the antibody coated nanoparticles are administered with checkpoint inhibitors, such as PD-1, PD-L1, CTLA-4, Jagged 1 inhibitor 15D11, etc. and Rock inhibitors (e.g., Fasudil or Botox) or Wnt inhibitor, such as niclosamide, ivernectin, etc., and for the future management of the tumor recurrences in the patient or treatment of metastatic disease.

In another embodiment, polymeric nanoparticles or polysaccharide or synthetic polymers conjugated with biomarkers are administered to enhance a vaccination effect and are taken up by antigen presenting cells.

In one embodiment, genetic analysis of the patient is performed to determine a sequence of the gene that is mutated. A sample of the patient's blood is analyzed for any of the following indicia of the presence or a neoplasm or a predisposition to a neoplasm: specific tumor biomarker(s), non-specific tumor biomarker(s), extravascular vesicles, circulating tumor cells, tumor micro RNA, micro DNA, or any other tumor indicator. RNA sequencing reflects the dynamic nature of gene expression for detection of RNA fragments, including mRNA, noncoding RNA, chimeric RNA, pathogen RNA, extracellular RNA, etc.

Examples of biomarkers have been previously disclosed. Other biomarkers include DNA hypermethylation, the presence of ZNF154 in colon, lung, breast, stomach, and endometrial tumor, and the stem cell marker NANOG, a mitochondrial oxidative phosphorylation/fatty acid oxidation molecule in highly malignant tumor-initiating stem-like cells (TICs) that reprograms mitochondrial metabolism.

Use of results from a patient's genetic analysis advantageously permits selection of a therapeutic agent, along with antibody-coated nanoparticles conjugated with thermosensitive polymers and thermotherapy, to provide the greatest efficacy against cancers that are smaller than 4 mm in diameter. In general, such cancers have not grown to a size whereby they show genetic differentiation of the cancer cells. Treatment of these small cancer cells can thus include treatment of the cancer stem cell(s). In one embodiment, nanoparticles activated by electromagnetic radiation, either in vitro or in vivo, enhance both gene transfer and cell proliferation of any desired cell, including stem cells In one embodiment, the patient's blood is processed to isolate the patient's own natural killer (NK) cells, i.e., a type of lymphocyte that is part of the patient's innate immune system, and dendritic cells, i.e., immune cells that process antigen material and present it on the cell surface to T cells of the immune system). NK cells and dendritic cells are isolated from a patient's blood using commercially available kits known in the art, e.g., EasySep™ and RosetteSep™ STEMCELL Technologies Inc., Tukwila Wash.; NK Cell Isolation Kit, Meltinyi Biotech, Bergisch Gladbach Germany. The natural killer cells/dendritic cells are rendered sensitized to the tumor in vitro. Sensitization is accomplished by co-culturing the patient's natural killer cells and/or dendritic cells with IL-2 and the antibody-coated nanoparticles containing the optional penetration-enhancing agents and/or thermosensitive polymers as previously described. The patient's sensitized natural killer cells/dendritic cells are then administered to the patient at intervals to provide a booster immune therapy, much as a vaccine booster injection does. The vaccine may be administered with or without VLPs. IL-2 is a protein produced by the T cells. When IL-2 is conjugated with the thermosensitive antibody coated nanoparticle, and administered with checkpoint inhibitors, such as PD-1, PD-L1, CTLA-4, Jagged 1 inhibitor, 15D11, etc. and Rock inhibitors, such as Fasudil or Botox, or Wnt inhibitors, such as niclosamide and ivermectin, or small molecule Wnt inhibitors upon controllable temperature release, IL-2 is systemically available to enhance a T-cell response in the patient by cell sensitization and proliferation as a vaccine or treatment of metastatic disease.

Thermal damage to the tumor cell membrane as a part of nanoparticle assisted thermotherapy releases antigens that, in vivo, activate and stimulate a dendritic cell immunogenic response. The activated dendritic cells induce a signal that additionally activates T cell-driven tumor cell damage or killing.

In one embodiment, the medium used to culture NK/dendritic cells contains viral like particles (VLP). The NK/dendritic cells pick up the VLP and enhance sensitization against the tumor. If tumor cell biopsy specimens are available, NK cells/dendritic cells are cultured from these biopsy specimens which additionally contain tumor lysate, killed circulating tumor (CT) cells, and their extracellular vesicles (ECV). In one embodiment, nanoparticles with thermosensitive polymers and conjugated with tumor antibody and VLP are administered to the patient intravenously, as the first step of tumor vaccination and therapy. The nanoparticles become attached to the tumor cells within a few minutes after administration.

In one embodiment, the tumor biomarkers from a patient's blood are identified, and anti-tumor antibodies are prepared, using conventional antibody techniques known in the art. The antibodies may be monoclonal, polyclonal, humanized, etc.; tumor antibodies also includes aptamers (oligonucleotide or peptides that bind to a specific target). The antibodies/aptamers are then coated on diagnostic or therapeutic nanoparticles or quantum dots, and conjugated with checkpoint inhibitors such as PD-1, PD-L1, CTLA-4, Jagged 1 inhibitor 15D11, etc. and Rock inhibitors, such as Fasudil, hydroxyl Fasudil, etc. botox, 3C exoenzyme etc. or Wnt inhibitor, such as niclosamide, as a vaccine or treatment of metastatic disease. which are then systemically administered to the patient. In vivo, the tumor-antibody-coated nanoparticles seek the tumor cells via the specificity of the anti-tumor antibody component. In one embodiment, adding a cell penetration enhancing agent to the polymer or other coating facilitates penetration of the tumor-antibody-coated nanoparticles into a tumor cell. Cell-penetration enhancing agents render the nanoparticle complex more biocompatible, and have been previously disclosed; they include cell penetrating peptide (CPP), activated CPP (APCC), (poly)ethylene glycol (PEG), biotin streptavidin, etc.

In one embodiment, as previously disclosed, the tumor-antibody-coated nanoparticles are also coated with a thermosensitive polymer that dissolves at a particular temperature, e.g., a polymer such as chitosan that dissolves at a temperature of 40° C.-43° C., and/or an arginine rich polymer, etc.

This coating, in addition to its thermosensitive properties, is administered with checkpoint inhibitors such as PD-1, PD-L1, CTLA-4, Jagged 1 inhibitor 15D11, etc. and Rock inhibitors, such as Fasudil, Botox, 3C exoemzyme, etc. or Wnt inhibitor, such as niclosamide, etc., and includes one or more medicaments, genes, etc. thus providing additional therapy to the patient upon administration and thermotherapy as a vaccine or treatment of metastatic disease. In one embodiment, adding a phospholipase, anti-phospholipid antibody, toxin (snake, scorpion, bee venom, etc. to the polymer or other coating enhances the damage to the cell membrane from an anti-tumor antibody coated nanoparticle. This beneficially increases the hyperthermal damage to cancer and other undesirable cells due to toxin release from the nanoparticles' coating of thermosensitive polymer at 40° C.-43° C.

In one embodiment, genes are provided that have a stimulatory action in response to light or ultrasound. An example of such a gene is the opsin gene and members of the opsin family. In this embodiment, such genes are provided to regulate cell membrane polarization and depolarization. Such genes can thus controllably create an action potential in the membrane of an excitable cell, such as a retinal cell, or a non-excitable cell such as a tumor cell. Controllable regulation may drive a permanent depolarization state to render the cells accessible to a desired medicament for cell destruction.

In one embodiment, combinations of genes can be used for controllable regulation. As an example, genes responding to light to produce action potential, combined with genes that can modifying a defective gene(s) in the cells of an organ, e.g., eye, brain, lung, spinal cord, peripheral nerve, lung, digestive tract, can be used in combination to facilitate regulation of actions including swallowing, breathing, gland secretion, etc., to restore the normal function of the organ. As another example, genes responding to light to produce an action potential, combined with inhibitory genes such as siRNA, RNAi, microRNA, can be used to inhibit tumor function by simultaneous depolarization of the tumor cells. These genes can additionally be combined with chemotherapeutic agent to work synergistically and damage the tumor cells.

Systemic administration of tumor antibody coated nanoparticles, coated with thermosensitive polymers and a cell penetration facilitating agent, targets the nanoparticles toward the tumor cell membrane. External energy is applied by a thermal delivery device that uses energy (electromagnetic radiation, microwave radiation, radiofrequency waves, an alternating magnet, focused ultrasound, etc.) to increase the temperature of the nanoparticle. The heated nanoparticle absorbs more energy than the tissue surrounding the nanoparticle. The temperature increase causes the nanoparticles to expand. Expansion of the nanoparticles creates a photoacoustic, thermoacoustic, or ultrasound wave, whose sound wave amplitude correlates with the amount of the temperature increase, i.e., the degree of the temperature rise.

In one embodiment, the ultrasound wave is recorded by a transducer and is transmitted to a unit to image the nanoparticle increase in temperature as one-, two- or three-dimensional images. This unit is connected to the thermal delivery device via a computer to maintain the amount of thermal energy needed for the time required to heat the nanoparticles to the desired temperature and for the desired time period and thus release medicament(s), gene(s), VLP, etc. These agents may also be against microorganisms, e.g., bacterial, viral, fungal, or parasitic agents, that have developed resistance to the therapeutic agents. For example, heated bacteria become more permeable to diffusion of appropriate medication; in contrast, non-heated bacteria remain resistant.

In one embodiment, nanoparticles coated with the desired antibody (e.g., anti-tumor antibody, anti-bacterial protein antibody, etc.) are administered to the patient to assure that the antibody-nanoparticle complex is in contact with the appropriate cells or tissues. It will be appreciated that the appropriate cells or tissues may include both circulating cells (e.g., ECV, endosomes, leukemic cells, etc.) and non-circulating cells (e.g., solid tumor).

In one embodiment, a small hand held photoacoustic unit with a small thermal delivery unit e.g. laser, microwave, or radiofrequency unit is placed externally over a subcutaneously located vessel to deliver a pulse of energy and to heat the nanoparticles attached to the circulating tumor cells and create a photoacoustic sound as they heat up. This records the sound wave each time a tumor cell passes by the external hand held unit, adjusts the temperature from 37° C.-43° C., thus assessing and quantifying non-invasively the circulating tumor cells using the hand held thermal imaging device.

In one embodiment, photoacoustic technology imaging is controlled to a low temperature of 37° C.-43° C., thus assessing and non-invasively measuring circulating cells using a hand held thermal imaging device. Imaging may be used in combination with any standard method, including but not limited to radiography, computed tomography (CT), magnetic resonance imaging (MRI), ultrasound, positron and other molecular imaging devices.

In one embodiment, nanoparticles are conjugated with VLP derived from plant viruses. In this embodiment, the VLP are used for cancer therapy by carrying sRNA, RNAi, etc. The host of these viruses are plants e.g. tobacco mosaic virus (TMV), bean yellow dwarf virus (BeYDV), etc., which cannot infect the patient. Thermal application of the antibody coated nanoparticles provides the control over when and where these particles are released to provide maximum benefit in immunotherapy. The VLP are generally immunogenic and do not require adjuncts to induce an immune response. These modified viruses are devoid of genetic components and cannot replicate in the body. However, if a specific gene of a specific protein e.g. an antibody, is conjugated with them and injected in the plant, the modified viruses produce large amounts of the antibody or protein in the plant, which can subsequently be extracted and used in human infective or non-infective diseases or to produce a vaccine to treat e.g. Alzheimer's disease etc. The thermal application at 41-43 degrees C. damages the VLP or other viruses and prevents their proliferation without reducing their immunogenicity. Once the antibody is produced, it can be used in diagnosing or guiding treatment to the affected area in combination with nanoparticles with or without VLP and drug delivery, and administering them with Rock inhibitors, such as Fasudil, botox 3 C exoenzyme, etc., or Wnt inhibitors, such as niclosamide to be used as a vaccine or treatment of metastatic diseases needed.

With respect to a gene(s) present in the polymer coating, e.g., an inhibitory gene such as siRNA, siDNA, RNAi, or an appropriate checkpoint inhibitor, may be used. Checkpoint inhibitors enhance cellular immune responses to tumor specific proteins in the cancer cells, as previously disclosed. In one embodiment, checkpoint inhibitors, such as PD-1, PD-L1, CTLA-4, Jagged 1 inhibitor 15D11, etc. and Rock inhibitors, such as Fasudil, botox or Wnt inhibitors, such as niclosamide or ivermectin, as a vaccine or for treatment of metastatic diseases needed or are combined with nanoparticle-assisted targeted immunotherapy as an adaptive T-cell transfer mechanism. These, along with the a CRISPR/cas9 or CRISPR interference (CRISPRi) complex, may perturb or modify the tumor genes.

With respect to a medicament(s), the medicament(s) would be released locally present in the polymer coating or pluralities of the antibody coated nanoparticles during thermotherapy. For a medicament that is a biologic, local release permits agents to be concentrated at the desired site without being released systemically resulting in systemic toxicity the medicament may otherwise cause. As one example, anti VEGF agents, TNF inhibitors, antineoplastic medications such as taxol, antimetabolites, anti-inflammatory agents, steroids, checkpoint inhibitors, such as PD-1, PD-L1, CTLA-4, Jagged 1 inhibitor 15D11, etc. and Rock inhibitors, such as Fasudil, 3C exoenzyme, Botox, etc., or Wnt inhibitors, such as niclosamide or ivermectin, antibiotics, antiviral agent, etc. can be used as a vaccine or for treatment of metastatic diseases and become localize specifically at a tumor or other site at significantly higher concentrations to stop tumor neovascular growth or damage the tumor etc., without causing the known systemic complications such as heart attack, intestinal bleeding, kidney disease, liver disease, or suppressing the normal humoral or cellular immune response of the body, etc. as seen in routine chemotherapy or immune therapy. As another example, release of phospholipase enzymes can create a hole in the membrane of tumors or other cells to provide or facilitate entry of a medicament(s) and/or gene(s) entry into a cell.

In the inventive precision nanoparticle assisted thermotherapy imaging (NATTI), the temperature of the tumor cell to which the nanoparticle is conjugated is controllably precisely increased. The temperature increases (a) releases a medicament(s) and/or gene(s) from a thermosensitive coating on the nanoparticle, and (b) enhances penetration of the medicament(s) and/or gene(s) through the open pores of the tumor cell membrane. NATTI technology includes a computer-controlled thermal energy delivery unit to ensure attainment of a desired increased temperature of the tumor for achieving the therapeutic goal. Controlling thermal energy delivery to achieve a temperature from 38° C. to 42° C. for drug delivery or more in the tumor-nanoparticle complex to a tumor, or to another tissue affected by a disease as directed by antibody binding to a corresponding antigen. It will be appreciated that the increased temperature may be maintained at the controlled desired level for any desired time interval, e.g., up to 1, 2, 3, 4, 5, 6, 7, 8, 9, 10, 11, 12, 13, 14, 15 minutes, or even longer, depending upon the need.

Typically, normal healthy cell membranes are comprised of the phospholipids phosphatidylserine (PS) and phosphatidylethanolamine (PE), which are located within the inner membrane and oriented toward the cell interior. However, for cancer cells, the orientations of PS and PE are flipped, so each oriented toward the cell exterior. The melting point of PS and PE is about 65° C.-70° C. degree. When the nanoparticles are heated to this temperature, the exposed PS and PE lipids of the cell membrane melt, and create a dehiscence in the cell membrane through which chemotherapeutic agents can freely flow into the tumor cell, killing the tumor cell.

For a medicament that is a chemotherapeutic agent, local release permits a higher concentration of a chemotherapeutic agent to be contained in the polymer coating, i.e., a supratherapeutic concentration, because it is confined to a localized site and would not result in systemic toxicity, yet still would achieve a higher therapeutic level at the tumor site. In one embodiment, a known existing antitumor chemotherapeutic agent is administered at a concentration that exceeds that of a concentration that would be administered under typical therapy, yet that does not result in patient toxicity. Similarly, one can use a toxic medicament(s) to locally perturb a cellular metabolic pathway or a specific cell cycle, e.g., local tumor cell perturbation. Such agents are generally not administered intravenously or orally because of their serious or fatal systemic toxicity and side effects. The concentration of the chemotherapeutic medicament(s) delivered by the inventive method is, in general, high locally, but less the $1/1000$ of the concentration that would be required if the medicament(s) were to be effective if delivered systemically.

Use of precision nanoparticle assisted thermotherapy and imaging (NATTI) may be used to fine-tune the approach to perturb survival mechanisms of tumors or other pathological cells. It will be thus appreciated that the inventive method may be used as a rapid en mass treatment of a cancer or an organ. For example, it may be used as a preliminary treatment in advance of other therapies that in general have severe debilitating systemic complications such as immune suppression, etc. and which may take longer to obtain approval for their administration. Thus, nanoparticle assisted thermotherapy and drug delivery NATTI avoids the chemotherapy complication of damaging the patient's immune system as a result of one or multiple chemotherapeutic agents used in these late metastatic cancer patients.

The nanoparticle assisted thermoacoustic imaging technology, along with thermal energy, drives the medicament(s), gene(s), VLP into the cancer cell, with simultaneous generation of an immune response to the cancer cell and inhibition of cancer cell proliferation by including siRNA, siDNA, etc., along with simultaneously enhancing gene therapy by conjugating a CRISPR/cas9 or CRISPRi complex to the nanoparticle to correct or inhibit a genetic component of a tumor. Once inside a cell, e.g., a tumor cell or the cell of an organ, the gene(s), along with the CRISPR/cas9 complex or CRISPRi, enter the cell nucleus or mitochondria and precisely modify the gene pool of those cells. The RNA-guided bacterial endonuclease Cas9 is the effector protein of the type II CRISPR/Cas9 system that detects and subsequently generates a double-strand break (DSB) in target DNA. This may treat a disease caused by a gene deficiency, or add a new useful gene(s), or remove and possible replace a gene, in the cell nucleus or the mitochondria.

The gene(s) and/or medicaments(s) may be delivered to a specific site, but not released in the circulation from the nanoparticles until reaching the required elevated temperature and after attaching to the tumor or other desired cells or desired location. It will be appreciated that the inventive method can be used in therapy for non-neoplastic diseases. As one example, the amyloid plaques present in Alzheimer's disease may be used to produce anti-amyloid plaque antibodies and treated by the inventive method. As another example, bacteria in patients with severe sepsis refractory to standard antibiotic therapy, e.g., patients with methicillin-resistant *Staphylococcus aureus* (MRSA) etc., may be used to produce anti-bacterial antibodies and treated by the inventive method. In this example, the method may be combined with extracorporeal treatment of blood, using a thermal energy delivery unit to provide electromagnetic radiation, radiofrequency waves, microwaves, focused ultrasound, an alternating magnetic field, etc., under the control of the described NATTI unit, to controllably achieve a temperature of 42° C.-45° C. to kill the bacteria prior to cooling the blood to the normal 37° C. prior to reinfusion to the patient.

In addition, increasing the temperature of the nanoparticles incrementally from 37° C.-43° C. allows precision nanoparticle assisted thermotherapy and imaging (NATTI) to release a gene(s) or medicament(s) from the nanoparticles. It will be appreciated that the method beneficially permits imaging a tumor or other desired cells, such as Alzheimer's plaques, that are present in a small lesion otherwise invisible by conventional imaging methods such as radiography.

The immune response is generated by two different mechanisms. One mechanism is by releasing the VLP, which then stimulate a cellular immune response at the site of the tumor. The other mechanism is by the thermotherapy-damaged tumor cells releasing their antigenic material in and beyond the surrounding tissues, creating a more active cellular immune response due to the additional tumor antigens present, and drawing the patient's immune cells, dendritic cell, T-lymphocytes, B-lymphocytes, macrophages, etc., to the tumor location. This mechanism also advantageously provides immune memory functioning as an internal vaccination method. Specifically, local release of antigens from damaged tumor cells enhances a patient's immune response to a large amount of other tumor cell associated antigens, creating a form of in vivo vaccination. Such vaccination can be provided as needed, e.g., annually, at specific intervals, upon specific events, etc. to prime the patient's immune cells against any future tumor cells, and protects against reappearance of any tumors with similar antigenic components. For example, vaccination may be administered annually or biannually or between annual and biannual administration indefinitely, unless new biomarkers are discovered in the patient, necessitating additional and/or earlier therapy.

In addition, the inflammatory process created as a result of the immune therapy and cellular response increases the temperature of the tissue involved, which is also recorded using photoacoustic technology imaging to image the tumor location and its potential metastatic lesions anywhere in the body.

This embodiment results in precise, local, internally-induced immunotherapy and simultaneous vaccination. The antigen, e.g. VLP, is delivered intravenously with thermosensitive polymers conjugated with antitumor antibody coated nanoparticles. The VLP are released from these nanoparticles only when the temperature of the nanoparticle is increased, and the nanoparticles are localized only at the tumor site, due to the specificity of the anti-tumor antibody with which the nanoparticles are conjugated.

As previously disclosed, various nanoparticle types, compositions, configurations, etc. are possible, including the following non-limiting examples: organic, synthetic, metallic, non-metallic, magnetic, non-magnetic, paramagnetic, etc., configurations such as a nanosphere, nanotube, nanoshell, nanocage, nanocarbon, etc., including quantum dots, dendrimers, liposomes, piezoelectric nanoparticles, etc.

In one embodiment, piezoelectric nanoparticles are stimulated by an ultrasonic unit, providing a therapeutic effect by inducing an electric current in cells. Depending upon the frequency, this exposure can kill cells on one hand, or it can enhance growth of specific cells on the other hand. Application of thermal energy at a frequency in the range of 1 Hz-20 Hz promotes cell growth. Application of thermal energy at a frequency greater than about 60 Hz damages cells. Cell death is desirable for treating pathologies such as cancer. However, cell proliferation is desirable to facilitating tissue regeneration. For example, in this embodiment, a patient with a stroke, or a myocardial infarction, or a spinal cord injury, may be treated to regenerate brain, heart, nerve tissue respectively. In this embodiment, the antibody used is targeted to the damaged cells, i.e., neurons, cardiac cells, etc., and treatment is with a pulsed frequency of 1 Hz-20 Hz or more is provided for 1 min-10 min. It will be appreciated that this embodiment permits stem cells to be controllably either stimulated or inhibited.

In one embodiment, the nanoparticle stimulates proliferation of in vitro cultured cells when the nanoparticle is exposed to and absorbs light pulses of low frequency, i.e., frequencies in the range of 1 Hz-20 Hz. Conversely, in one embodiment, the nanoparticle inhibits cell proliferation when the nanoparticle is exposed to and absorbs light pulses of very high frequency, i.e., frequencies in the range of >30 Hz-100 Hz). Thus, selecting the frequency of the thermotherapy, and thus the frequency to which the tumor antibody-coated nanoparticles are exposed, adds to the mechanisms of therapy the patient receives if the light pulses are at low frequencies, i.e., no higher than about 20 Hz.

In one embodiment, after sensitization of the immune cells with the tumor antigen, functionalized quantum dots with antibody coated against cell membrane of immune cells is added so that the cell membranes of the immune cells carry a marker that can be made visible with specific wavelength of light extracorporally.

In one embodiment, antibody coated nanoparticles are conjugated with thermosensitive polymers containing VLP/medication/genes, and administered with checkpoint inhibitors, such as PD-1, PD-L1, CTLA-4, Jagged 1 inhibitor 15D11, etc. and Rock inhibitors, such as Fasudil, botox, or Wnt inhibitors, such as niclosamide etc., and intravenously administered to a patient at far lower level than would be toxic to the body (i.e., $\frac{1}{10}$ to $\frac{1}{100}$ of the non-toxic dose approved by the FDA). The VLP are released from the thermosensitive nanoparticles by thermal application at temperatures of 41° C.-43° C. The increase in temperature is achieved using, e.g., activation by light, electromagnetic radiation, microwave radiation, radiofrequency waves, focused ultrasound, or alternating magnetic field to preferentially heat the nanoparticles because of their high surface to volume ratio, and because the selected molecular composition of the nanoparticles preferentially absorbs more thermal energy than the surrounding normal cells. The tumor cells to which the nanoparticles are attached are also heated. The thermal energy damages also the VLP without reducing its immunogenicity at temperature or 41-43 degrees C. so that there is no chance of multiplication of the VLP in the body.

In one embodiment, the increase in the temperature of the nanoparticles results in their thermal expansion. Thermal expansion of the nanoparticles produces an ultrasonic wave that passes through the body, is captured by a receiver, the ultrasonic pulse is converted and amplified by an ultrasonic, photoacoustic, or thermoacoustic unit, imaged as a thermoacoustic signal or as nanoparticle assisted thermoacoustic signal, and converted by a computer to images, in one-, two-, or three-dimensions, of the temperature and the lesion.

In one embodiment, the photoacoustic or nanoparticle assisted thermoacoustic unit controls the thermal energy delivery unit via a processor to maintain the temperature of the nanoparticles at a predetermined temperature as a closed circuit once the nanoparticles have attached to the tumor cells. An increase in the temperature to which the nanoparticles are exposed, i.e., at the nanoparticle level, from 37° C. to 41° C.-43° C. melts the thermosensitive polymers coating the nanoparticles, releasing under control the conjugated VLP, medication/gene which are attached to the thermosensitive antibody coated nanoparticles locally at the desired site. This method is particularly effective in small tumors, i.e., tumors less than 4 mm in diameter, because the tumor stem cells are still present at the original tumor site and can be simultaneously killed and eliminated before metastasis has occurred.

In one embodiment, a plurality of the antibody-coated nanoparticles are injected into a patient's circulation with the cultured and tumor-sensitized NK cells/dendritic cells to target the tumor. It will be appreciated that such thermal damage to tumor cells, and a NK cellular response, generates and releases relatively large quantities of lytic enzymes and other cellular contents. In the case of smaller tumors, the released substances are of smaller quantities, but for larger tumors it become necessary to remove them from the blood, by plasmaphoresis, plasma exchange etc. these substances released into a patient's circulation, may be thought of as cellular debris or detritus, to prevent an immunogenic or cytokine storm in the body.

In one embodiment, the patient receiving the inventive therapy undergoes plasmapheresis to remove, e.g., such cytokines, enzymes, dead cells, etc. from the circulation. Plasmaphoresis is a known method to remove components from blood plasma. Because the patient's plasma is treated extracorporeally, then reinfused, in contrast to reinfusing only cellular components of the patient's blood, plasmaphoresis also beneficially detoxifies the patient's plasma without compromising blood volume and with minimal or no fluid loss. This technique avoids the serious complications and side effects of simply returning the cellular components of the blood to the patient. Additionally, all precautions are observed to avoid hypotension and loss of calcium ions in the process of citrate anticoagulation that this procedure requires. The patient can be treated initially with presently available anticoagulants such as heparin, coumadin, etc., which can be immediately neutralized post-procedure. Neutralization uses standard techniques known in the art, such as calcium, etc. Hemofiltration treatment is performed with activated carbon, treatment on non-ionic exchange resins, etc. for removing free toxin and also toxin bound with plasma proteins, etc. as in renal dialysis methods. The process may be instituted or repeated as needed, e.g., if the tumor reappears. The addition of Rock inhibitors or Wnt inhibitors along with other therapeutic agents can reduce the ever inflammatory response seen in immune therapy or an auto immune disease.

In one embodiment, to prevent a severe autoimmune response after tumor immunotherapy, one uses extracorporeal plasmapheresis. A strong pulse of light energy is applied to a tube containing blood cells to achieve a temperature up to 60° C. to kill immune cells containing quantum dots. The blood is then passed through a dielectrophoresis system to characterize and remove dead or live T-cells, sensitized killer cells, and tumor cells, prior to re-infusing the same blood or performing a blood transfusion in the patient while simultaneously administering immunosuppressive agents, including a biologic, to reduce the severe autoimmune response often seen after tumor immunotherapy.

The size of the nanoparticle may vary, and may vary depending on the site of therapy and imaging as well as other factors. In one embodiment, the nanoparticle size ranges from 1 nm to 999 nm or more. In one embodiment, the nanoparticle size ranges from 1 nm to 20 nm, which is ideal for use in the eye and central nervous system to permit the nanoparticle access to the intercellular space, and also ideal for renal clearance without generating systemic side effects. Nanoparticles having a size less than 10 nm in diameter, and not bound to a tumor, i.e., nanoparticles that are free in the circulation, undergo rapid renal elimination from the body within a few hours of administration. Only nanoparticles attached to the tumor cells remain in the body. This results in a novel form of simultaneous local thermotherapy and vaccination.

The localized thermotherapy component of the method damages the tumor cells, thus disseminating tumor cell-associated antigens into the circulation, generating a cellular immune response to the various tumor biomarkers that were originally present. This dual thermotherapy and cellular response augments the effect of both immunotherapy and thermotherapy. The inventive method augments immunotherapy methods that relied on T-cells that had been sensitized to just a few tumor markers, or that relied only on checkpoint inhibitors to prevent the tumor cells' sequestration from T-lymphocytes. Previous methods of tumor vaccination used intradermal or subcutaneous antigen administration, with the antigen taken up by antigen presenting cells, e.g., dendritic cells, to generate specific killer cells only at a location remote from the specific tumor site. The inventive method augments the previous immunotherapy methods by combining immunotherapy to act synergistically with thermotherapy locally at the tumor site, providing exposure of the entire body to therapeutic agents or checkpoint inhibitors that causes immune suppression or auto-immune disease.

In one embodiment, cultured killer cells sensitized to a tumor are administered simultaneously with the anti-tumor antibody coated nanoparticle-conjugated VLP to attack the tumor cells by the patients t-lymphocytes etc. and remove the dead tumor cells. For example, an intradermally administered antitumor antibody-coated nanoparticle with VLP can be administered with checkpoint inhibitors such as PD-1, PD-L1, CTLA-4, Jagged 1 inhibitor 15D11, etc., and Rock inhibitors, such as Fasudil, botox or Wnt inhibitors, such as niclosamide, in subsequent rounds of therapy during a postoperative period to induce an immune response as needed. This embodiment decreases the likelihood of, or prevents potential recurrences of the tumor or treats a recurrence of a tumor as a vaccination or therapy in recurrences. Since tumor recurrences are generally non-sensitive to ordinary therapy, it is important that vaccination is done along with the checkpoint inhibitors to be able to attack the tumor and the cell recurrences that potentially have survived the previous therapy addition or Rock inhibitors or Wnt inhibitors reduces excessive inflammatory disease and discourage tumor cell proliferation.

In one embodiment for use in larger tumors of a sufficient size for biopsy, an antibody directed to the tumor lysate (TL) is used as a source of tumor-associated antigens (TAAs), and is conjugated with the nanoparticles for generating therapeutic anti-tumor immune responses. One can generate in vivo immunity against multiple TAA simultaneously from the killed or damaged tumor cells during the thermotherapy. This embodiment broadens the repertoire of TAA-specific T-cell clones available for activation or therapy of these tumors.

In one embodiment, after an initial thermotherapy procedure, a blood sample is obtained from the patient. This blood sample contains released tumor antigens that are recoverable prior to treatment by the inventive method using various immunoassays or methods of searching for biomarkers. The tumor antigens are then used to generate, in vitro, additional T-cells that are sensitized to many TAA for future use in, along with VLP for vaccination, and are administered with checkpoint inhibitors, such as PD-1, PD-L1, CTLA-4, Jagged 1 inhibitor 15D11, etc., and Rock inhibitors, such as Fasudil, etc. or Wnt inhibitors, such as niclosamide, etc. to the same patient to enhance the immune response as a vaccine or to treat potential recurrences of the same tumor.

In one embodiment, immunostimulatory oligonucleotide-loaded cationic graphene oxide, carbon nanotube, gold/iron, iron/zinc oxide, or cadmium sulfate nanoparticles are combined with photothermally enhanced immunogenicity to achieve combined thermo-immune therapy. In one embodiment, RNA oligonucleotides/graphene or graphene oxide, or long double stranded RNA/graphene oxide induces a controlled immunostimulation in combination with oncogene silencing RNAi.

Nanoparticles, dendrimers, carbon nanotubes, lipid-based carriers, micelles, gold nanoshells/nanocages, PLGA, chitosan, PEI cationic lipid, and cationic polymers are useful gene therapy, gene delivery, and immuno therapy. These have the advantages of being easily prepared, biodegradable, non-immunogenic, non-toxic, and water soluble.

EXAMPLE 1

T cells and dendritic cells are obtained from a patient's blood, and grown in culture along with a tumor or other antigen, plus nanoparticles coated with thermosensitive polymers conjugated with antigen and VLP using culture methods known in the art.

The nanoparticle complex is injecting them along with checkpoint inhibitors and IL-2. The inventive method is applied, killing tumor cells, and increasing the response of T-cells and dendritic cell.

The patient's blood is assessed for new biomarkers from the dead cells.

The cultured T-cells and dendritic cells are harvested, along with the nanoparticle-coated antigen plus VLP or RNA or DNA phages. These are stored under appropriate conditions, and reinjected into the patient with low dose coated nanoparticles or systemic medications to be administered with checkpoint inhibitors such as PD-1, PD-L1, CTLA-4, Jagged 1 inhibitor 15D11, etc. and Rock inhibitor, Fasudil or Wnt inhibitor such as niclosamide as needed, e.g., semi-annually, annually, biannually, etc. as vaccination or in tumor recurrences in metastatic disease with repetition as needed. This is followed up with counting or quantifying circulating DNA, exosomes or circulating cells to recognize potential tumor recurrences.

EXAMPLE 2

A checkpoint inhibitors and rock inhibitors, e.g., Botox up to 50-100 picograms (pg), or 100 picograms (pg) to 1 nanogram (ng) or more or fasudil from 100 picograms (pg) to 10 nanograms (ng) or 50 nanograms (ng) to 1 milligrams (mg) or Wnt inhibitors, e.g., niclosamide is added to a thermosensitive polymer conjugated with and antibody coated pluralities of nanoparticle for controlled release with the checkpoint inhibitor using the inventive controlled thermotherapy, NATTI, to release the medication locally at temperature of 41-43 C degree along immune stimulators such as VLP to treat a patient with breast, colorectal, glioblastoms, prostate, eye or skin melanomas, pancreatic, lung cancer, and/or ovarian cancer etc. A checkpoint inhibitor, such as nivolumab or PD-1L, CTLA-4, Jagged 1 inhibitor 15D11, etc. and Rock inhibitors, such as Fasudil or botox, or Wnt inhibitors, such as niclosamide or ivermectin, is combined with pluralities of antibody coated nanoparticle assisted targeted immunotherapy for adaptive T-cell transfer to overcome the limitations of standard immunotherapy and prevent a cytokine storm. In one embodiment the Rock inhibitor Fasudil can be taken orally at the dose of 40-80 mg as needed and niclosamide 1-2 gram once or repeated in a week ivermeting also can be given orally at a dose of 1 gram orally for a period of time during and shortly after thermotherapy for a few days as needed.

EXAMPLE 3

Nanoparticles are conjugated with a chimeric receptor, a CD19 protein that is found only on B cells, along with the T-cells cultured in vitro that expresses a chimeric antigen receptor (chimeric antigen receptor T (CAR T)-cells) to target abnormal B cells seen in leukemia along with PD-1L, CTLA-4, Jagged 1 inhibitor 15D11, etc. and Rock inhibitors, such as Fasudil or botox, or Wnt inhibitors, such as niclosamide. The reappearance of new biomarkers as neoantigens in these patients can be also treated in the postoperative period using the inventive method repeated therapy as vaccination along with Rock inhibitor encourage the abnormal mature cells to undergo apoptotic degeneration rather cell proliferation with abnormal genetic changes which is characterized by the tumors occurring as a result of aging process and not a pre-existing genetic mutation.

Plasmaphoresis is simultaneously performed or performed after treatment.

This example treats acute and chronic hematologic malignancies such as acute lymphoblastic leukemia, non-Hodgkin lymphoma, chronic lymphocytic leukemia, chronic myelogenous leukemia, etc.

EXAMPLE 4

Pluralities of antibody coated nanoparticles are conjugated with all-trans retinoic acid (ATRA) and arsenic trioxide to target leukaemia cells in acute promyelocytic leukemia and used in the inventive method. The all-trans retinoic acid is released at the site of the tumor without exposing the entire body to the toxic medication, simultaneously, plasmophoresis is performed to clear all toxin released in the blood, along with leukemic cells. It is appreciated that other blood cell cancers are removed in the same session.

EXAMPLE 5

In a patient with a hematologic malignancy that is resistant to chemotherapeutic agents or immune therapy, NATTI is performed with gene delivery, along with chemotherapeutic agents, to target all immune cells initially without subjecting the patient to systemic heavy chemotherapy, followed by bone marrow transplantation, without exposing the entire body to systemic chemotherapy.

EXAMPLE 6

Pluralities of antibody coated nanoparticles are conjugated with RNA that contains an aptamer, ribosomes, and siRNA in a thermosensitive polymer and administered to using NATTI to target specific tumor cells.

EXAMPLE 7

The microenvironment of the cancer cell is modified by delivering medicaments that block the uptake of exosomal signals and prevent the uptake of ECV. Such medications include choloroquine, heparin, cytochalasin D, and ethylisopropyl amiloride are conjugated with polymeric coating and conjugated with antibody coated nanoparticles administered to the patient and released with NATTI. These medications are approved for patient use. The medicaments are provided using NATTI in conjunction with chemotherapeutic agents and rock inhibitors.

EXAMPLE 8

The inventive method provides nanoparticle assisted localized immunothermotherapy and thermotherapy for delivery of customized vaccines with or without VLP to target core mutations in a patient. The immune cells or T-cells that can attack those core mutations are identified via a cancer biomarker. The immune cells or T-cells are then cultured with the nanoparticles coated with thermosensitive particles and VLP and IL-2. The antibody coated nanoparticles with checkpoint inhibitors, such as PD-1, PD-L1, CTLA-4, Jagged 1 inhibitor 15D11, etc., and Rock inhibitor, such as Fasudil or Botox etc., or Wnt inhibitor, such as niclosamide, etc., are injected into the patient, controllably heated using a thermal energy source, and imaged, for specific patient, or those with metastatic disease or recurrences as immunotherapy, such as in breast cancer, prostate cancer, glioblastoma, lung cancer, melanoma, ovarian cancer, pancreatic cancer, intestinal or colon cancer, etc.

EXAMPLE 9

Antibody coated nanoparticles are conjugated with RNA phage VLP, which is generally stable. VLPs of the related RNA phage PP7 are crosslinked with inter-subunit disulfide bonds, rendering them significantly more stable. They exhibit high immunogenicity. Such nanoparticles complement the inventive NATTI technology and can be employed in anti-cancer and antibacterial treatment. Lytic phages attach to receptors on the bacterial surface, inject their genetic material through the bacterial membrane, and overtake the bacterium's transcription and translation machinery to synthesize new phages. The application of thermotherapy damages all VLP, phages, virocides or foreign protein and eliminate their future growth and potential adverse reactions.

EXAMPLE 10

To prevent a severe autoimmune response after tumor immunotherapy, before extracorporeal plasmapheresis, one uses the nanoparticle assisted thermotherapy and imaging system to apply heavy thermal energy to a tube containing blood cells and to achieve a temperature as high as 60° C. to kill the sensitized immune cells containing nanoparticles. Blood is then passed through a dielectrophoresis system to characterize and remove dead or live T-cells, sensitized killer cells, and dead tumor cells prior to re-infusing blood in the patient while simultaneously administering immunosuppressive agents and Rock inhibitors, including biologics. This reduces the severe autoimmune response often seen after tumor immunotherapy.

The embodiments shown and described in the specification are only specific embodiments of the inventor who is skilled in the art and are not limiting in any way. Therefore, various changes, modifications, or alterations to those embodiments may be made without departing from the spirit of the invention in the scope of the following claims. The references cited are expressly incorporated by reference herein in their entirety.

The invention claimed is:

1. A cancer therapeutic method comprising administering to a patient having a tumor a combination of thermotherapy and immunotherapy, where
    thermotherapy comprises systemically administering a plurality of tumor-antibody-coated nanoparticles coated with a thermosensitive polymer, the thermotherapy further comprises heating the tumor-antibody-coated nanoparticles using an energy source at the site of the tumor so as to damage one or more tumor cell membranes and release antigenic material in vivo that activates and stimulates an immunogenic response of the patient at the site of the tumor; and
    immunotherapy comprises systemically administering the patient's natural killer (NK) cells/dendritic cells pre-sensitized in vitro to the tumor, and further administering tumor-antibody-coated nanoparticles conjugated with viral-like particles (VLP) while simultaneously administering tumor-antibody-coated nanoparticles conjugated with at least one of checkpoint inhibitors, Rock inhibitors, or Wnt inhibitors to prevent the proliferation of tumor cells or metastatic cells, and/or prevent the tumor cells or metastatic cells from being disguised from T-lymphocytes of the patient or the patient's natural killer (NK) cells.

2. The method of claim 1 where the tumor-antibody-coated nanoparticles are conjugated with checkpoint inhibitors, the checkpoint inhibitors selected from the group consisting of PD-1, PD-L1, CTLA-4, jagged 1 inhibitor 15D11, and combinations thereof.

3. The method of claim 1 where the tumor-antibody-coated nanoparticles are conjugated with Rock inhibitors, the Rock inhibitors selected from the group consisting of Fasudil, exoenzyme, Y27632, Botox, and combinations thereof, the Rock inhibitors reducing an inflammatory response of the patient and preventing an autoimmune reaction or cytokine storm.

4. The method of claim 1 where the tumor-antibody-coated nanoparticles are conjugated with Wnt inhibitors, the Wnt inhibitors selected from the group consisting of niclosamide, ivermectin, and combinations thereof.

5. The method of claim 1 further comprising the step of:
    repeating administration of the tumor-antibody-coated nanoparticles conjugated with the VLP and the tumor-antibody-coated nanoparticles conjugated with the at least one of the checkpoint inhibitors, Rock inhibitors, or Wnt inhibitors once or twice a year, thereby reducing an autoimmune reaction; and
    further administering tumor-antibody-coated nanoparticles conjugated with polylactic acid or polyglycolic acid.

6. The method of claim 1 where the tumor-antibody-coated nanoparticles administered during thermotherapy are conjugated with a medication, and where thermotherapy includes exposing the tumor-antibody-coated nanoparticles and medication to a light pulse at a frequency in the range of 20 Hz to 60 Hz to decrease proliferation of the tumor cells.

7. The method of claim 1 where immunotherapy is administered at intervals to the patient after the initial therapy acting as a booster to the original immunotherapy and reduce or prevent tumor recurrences at a same or different site.

8. The method of claim 1 where immunotherapy further comprises obtaining NK cells/dendritic cells grown in culture under light pulses with a tumor biomarker from blood or a tumor biopsy specimen containing tumor lysate, killed circulating tumor cells (ct cell), and tumor extracellular vesicles (ECV).

9. The method of claim 1 where thermotherapy includes exposing the tumor-antibody-coated nanoparticles to a light pulse at a frequency in the range of 20 Hz-60 Hz to decrease proliferation of the tumor cells.

10. The method of claim 1 where the step of heating the tumor-antibody-coated nanoparticles using the energy source comprises using a thermoacoustic unit to control a thermal energy delivery unit using a processor to maintain the tumor-antibody-coated nanoparticles at a predetermined temperature as a closed circuit once the tumor-antibody-coated nanoparticles have attached to the tumor cells, then controllably increasing the temperature to which the tumor-antibody-coated nanoparticles are exposed from 37° C. to 41° C.-43° C. for the predetermined time period resulting in melting the thermosensitive polymer coating of the tumor-antibody-coated nanoparticles, and further releasing under control a medication or gene, which are attached to the thermosensitive tumor-antibody-coated nanoparticles locally at the desired site.

11. The method of claim 1 where the anti-tumor antibody is specific for at least one tumor biomarker in the patient's blood.

12. The method of claim 1 further comprising performing precision nanoparticle assisted thermotherapy and generating a photoacoustic image of the cells to which the nanoparticles bind at an early cellular stage of the tumor, the tumor having a size between one and two millimeters in diameter not easily detectable by radiographic imaging.

13. The method of claim 1 where the tumor-antibody-coated nanoparticles administered during thermotherapy are further conjugated with a toxin to further damage the one or more tumor cell membranes, the toxin selected from the group consisting of snake venom, scorpion venom, and bee venom.

14. The method of claim 1 where the tumor-antibody-coated nanoparticles administered during thermotherapy are further conjugated with cell penetrating peptides (CPP) or activatable cell penetrating peptides (ACPP) to facilitate penetration of the tumor-antibody-coated nanoparticles into the tumor cells.

15. The method of claim 1, further comprising:
applying light energy to a tube containing the patient's blood cells post-therapy to achieve a temperature up to 60° C. to kill immune cells containing nanoparticles;
passing the pulsed blood cells through a dielectrophoresis system to characterize and remove dead or live T-cells, sensitized killer cells, and tumor cells; and
re-infusing the dielectrophoresis treated blood in the patient while simultaneously administering immunosuppressive agents, thus reducing the likelihood of a severe post-therapy autoimmune response in the patient.

16. A cancer therapeutic method comprising administering to a patient having a tumor a combination of thermotherapy and immunotherapy, where
thermotherapy comprises systemically administering a plurality of tumor-antibody-coated nanoparticles coated with a thermosensitive polymer, the thermotherapy further comprises heating the tumor-antibody-coated nanoparticles using an energy source at the site of the tumor so as to damage one or more tumor cell membranes and release antigenic material in vivo that activates and stimulates an immunogenic response of the patient at the site of the tumor;
immunotherapy comprises systemically administering the patient's natural killer (NK) cells/dendritic cells pre-sensitized in vitro to the tumor; and
the method further comprises performing precision nanoparticle assisted thermotherapy and generating a photoacoustic image of the cells to which the tumor-antibody-coated nanoparticles bind at an early cellular stage of the tumor, the tumor having a size between one and two millimeters in diameter not easily detectable by radiographic imaging.

* * * * *